United States Patent [19]
Hammerslag

[11] Patent Number: 5,843,124
[45] Date of Patent: Dec. 1, 1998

[54] SURFACE OPENING ADHESIVE SEALER

[75] Inventor: Julius G. Hammerslag, San Juan Capistrano, Calif.

[73] Assignee: Hemodynamics, Inc., San Clemente, Calif.

[21] Appl. No.: 701,808

[22] Filed: Aug. 21, 1996

Related U.S. Application Data

[63] Continuation-in-part of Ser. No. 314,049, Sep. 28, 1994, Pat. No. 5,653,730, which is a continuation-in-part of Ser. No. 127,769, Sep. 28, 1993, abandoned.

[51] Int. Cl.$^6$ .................................................. A61B 17/00
[52] U.S. Cl. ........................ 606/214; 606/194; 178/898
[58] Field of Search .................................. 606/212–214, 606/151, 194, 92–95, 117, 191; 128/673, 672, 748, 898, 899; 604/118, 121, 11–18, 96, 98, 310, 311; 272/510; 401/263

[56] References Cited

U.S. PATENT DOCUMENTS

| | | |
|---|---|---|
| 55,008 | 5/1866 | Gannett . |
| 1,071,063 | 8/1913 | Lee . |
| 1,083,532 | 1/1914 | Grayham . |
| 1,577,465 | 3/1926 | Houge . |
| 2,012,164 | 8/1935 | Gordon . |
| 2,388,321 | 11/1945 | Gereke . |
| 2,636,647 | 4/1953 | Covitt et al. . |
| 2,752,920 | 7/1956 | Kurkijian . |
| 3,220,413 | 11/1965 | Sunnen . |
| 3,223,083 | 12/1965 | Cobey . |
| 3,527,841 | 9/1970 | Wicker, Jr. et al. . |
| 3,559,652 | 2/1971 | Banitt et al. . |
| 3,577,516 | 5/1971 | Gould et al. . |
| 3,772,599 | 11/1973 | Robertson et al. . |
| 4,414,976 | 11/1983 | Schwartz et al. . |
| 4,545,374 | 10/1985 | Jacobson . |
| 4,578,055 | 3/1986 | Fischer . |
| 4,606,337 | 8/1986 | Zimmerman et al. . |
| 4,806,614 | 2/1989 | Matsuda et al. . |
| 4,829,099 | 5/1989 | Fuller et al. . |
| 4,900,303 | 2/1990 | Lemelson ............................... 606/213 |
| 4,909,251 | 3/1990 | Seelich . |
| 4,981,483 | 1/1991 | Akimova et al. . |
| 4,993,948 | 2/1991 | Cameron et al. . |
| 5,011,493 | 4/1991 | Belykh et al. . |
| 5,021,059 | 6/1991 | Kensey et al. . |
| 5,141,522 | 8/1992 | Landi . |
| 5,156,613 | 10/1992 | Sawyer . |
| 5,158,542 | 10/1992 | Lazarus . |
| 5,201,712 | 4/1993 | Bryant . |
| 5,201,745 | 4/1993 | Tayot et al. . |

(List continued on next page.)

FOREIGN PATENT DOCUMENTS

| | | |
|---|---|---|
| WO/9014810 | 12/1990 | WIPO . |
| WO/9107136 | 5/1991 | WIPO . |
| WO/9221297 | 12/1992 | WIPO . |
| WO/9306878 | 4/1993 | WIPO . |
| WO/9308746 | 5/1993 | WIPO . |

OTHER PUBLICATIONS

*Long Term Pathological Follow–Up of Cerebral Arteriouvenous Malformations Treated By Embolization with Bucrylate*, By Harry V. Vinters et al., The New England Journal of Medicine, Feb. 29, 1986, pp. 447–483.

*Primary Examiner*—Jeffrey A. Schmidt
*Attorney, Agent, or Firm*—Knobbe, Martens, Olson & Bear, LLP

[57] ABSTRACT

Disclosed is a device for delivering tissue adhesives and/or sealant patches to a surface which covers or surrounds a perforation in a lumen, cavity or organ, or potential lumen or cavity, within a human or other animal. Also disclosed is a method of delivering tissue adhesives and/or sealant patches to a surface which covers or surrounds a lumen, cavity or organ, or potential lumen or cavity. The method is particularly suited to sealing perforations in vascular walls, such as after arterial access for Percutaneous Transluminal Coronary Angioplasty (PTCA), Percutaneous Coronary Angiography and Percutaneous Coronary Atherectomy and other diagnostic and therapeutic procedures.

22 Claims, 20 Drawing Sheets

U.S. PATENT DOCUMENTS

| | | |
|---|---|---|
| 5,209,776 | 5/1993 | Bass et al. . |
| 5,219,328 | 6/1993 | Morse et al. . |
| 5,222,939 | 6/1993 | Tiefenbrun . |
| 5,236,455 | 8/1993 | Wilk et al. . |
| 5,236,563 | 8/1993 | Loh . |
| 5,292,333 | 3/1994 | Johnson . |
| 5,312,355 | 5/1994 | Lee . |
| 5,320,639 | 6/1994 | Rudnick ................ 606/213 |
| 5,324,305 | 6/1994 | Kanner . |
| 5,324,306 | 6/1994 | Makower et al. ............. 606/213 |
| 5,383,896 | 1/1995 | Gershony et al. . |
| 5,383,897 | 1/1995 | Wholey . |
| 5,391,183 | 2/1995 | Janzen ................ 606/213 |
| 5,395,383 | 3/1995 | Adams et al. . |
| 5,397,311 | 3/1995 | Walker et al. . |
| 5,431,639 | 7/1995 | Shaw ................ 606/213 |
| 5,437,631 | 8/1995 | Janzen ................ 606/214 |
| 5,441,517 | 8/1995 | Kensey et al. ............ 606/213 |
| 5,529,577 | 6/1996 | Hammerslag . |

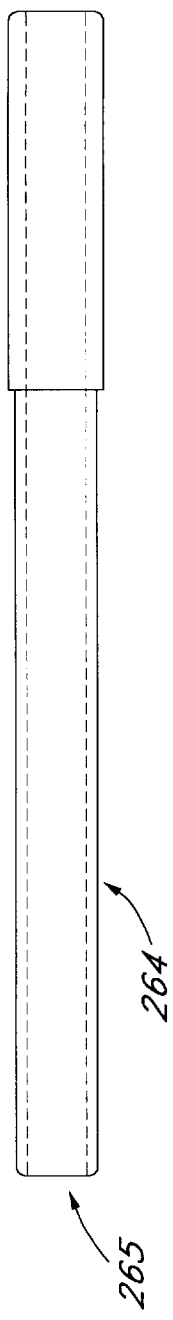
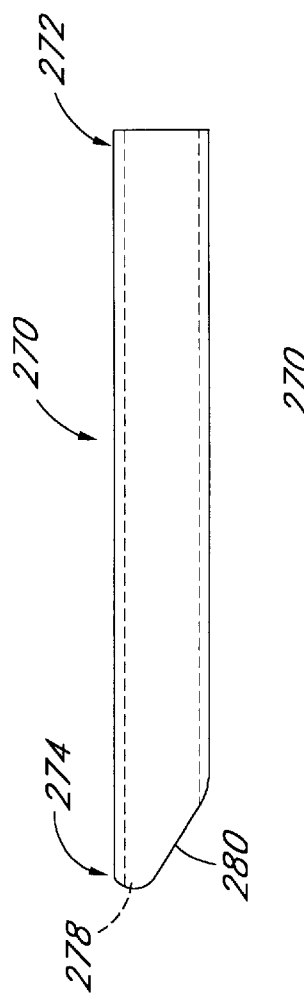
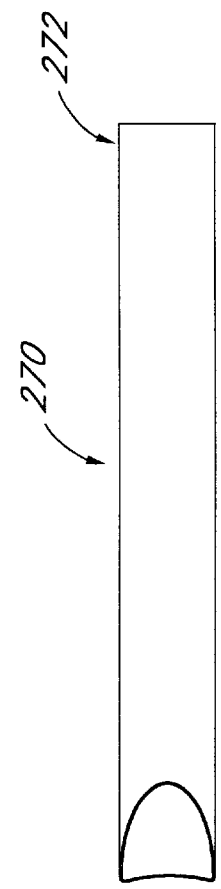
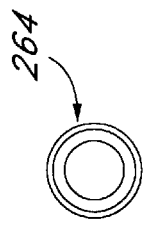

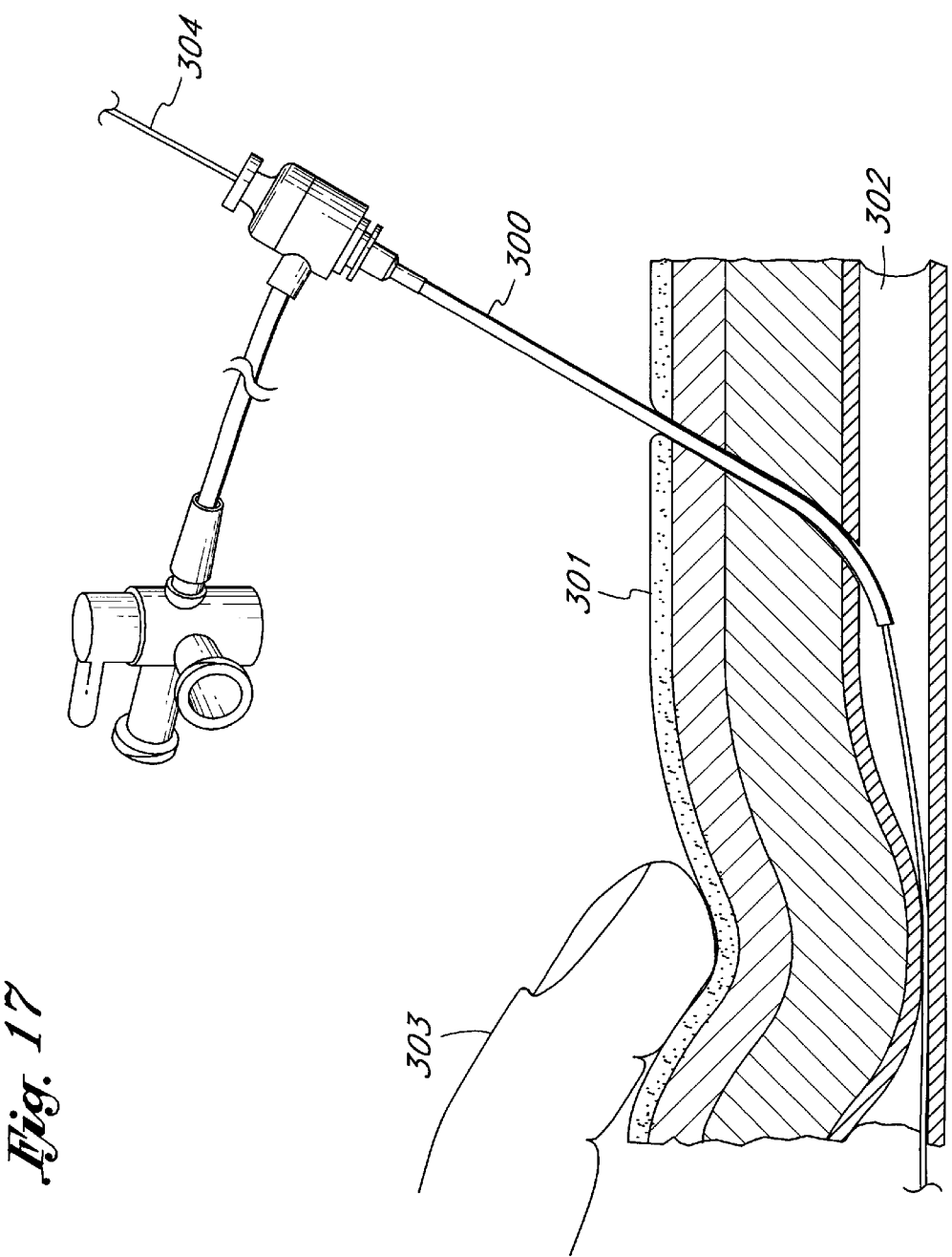

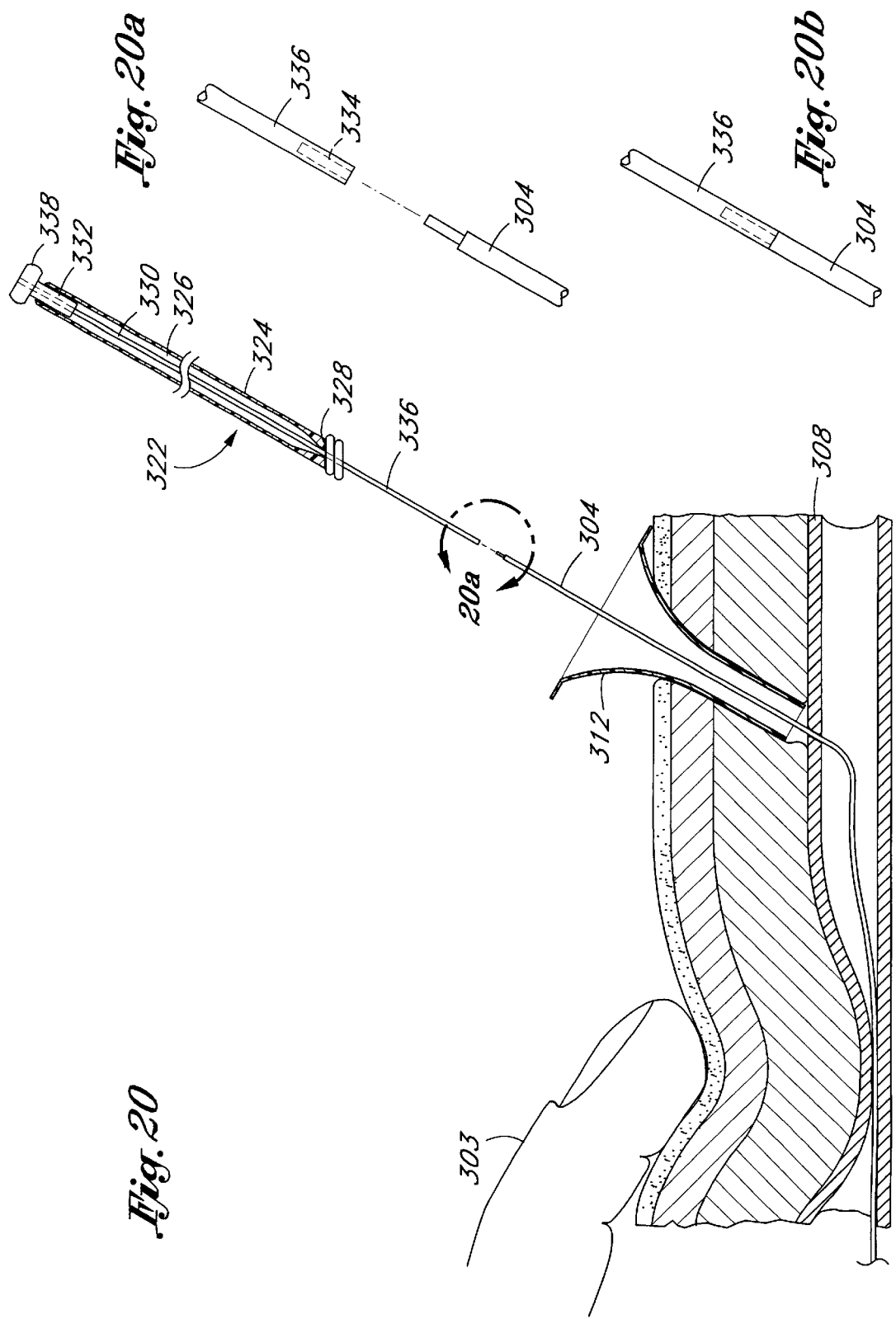

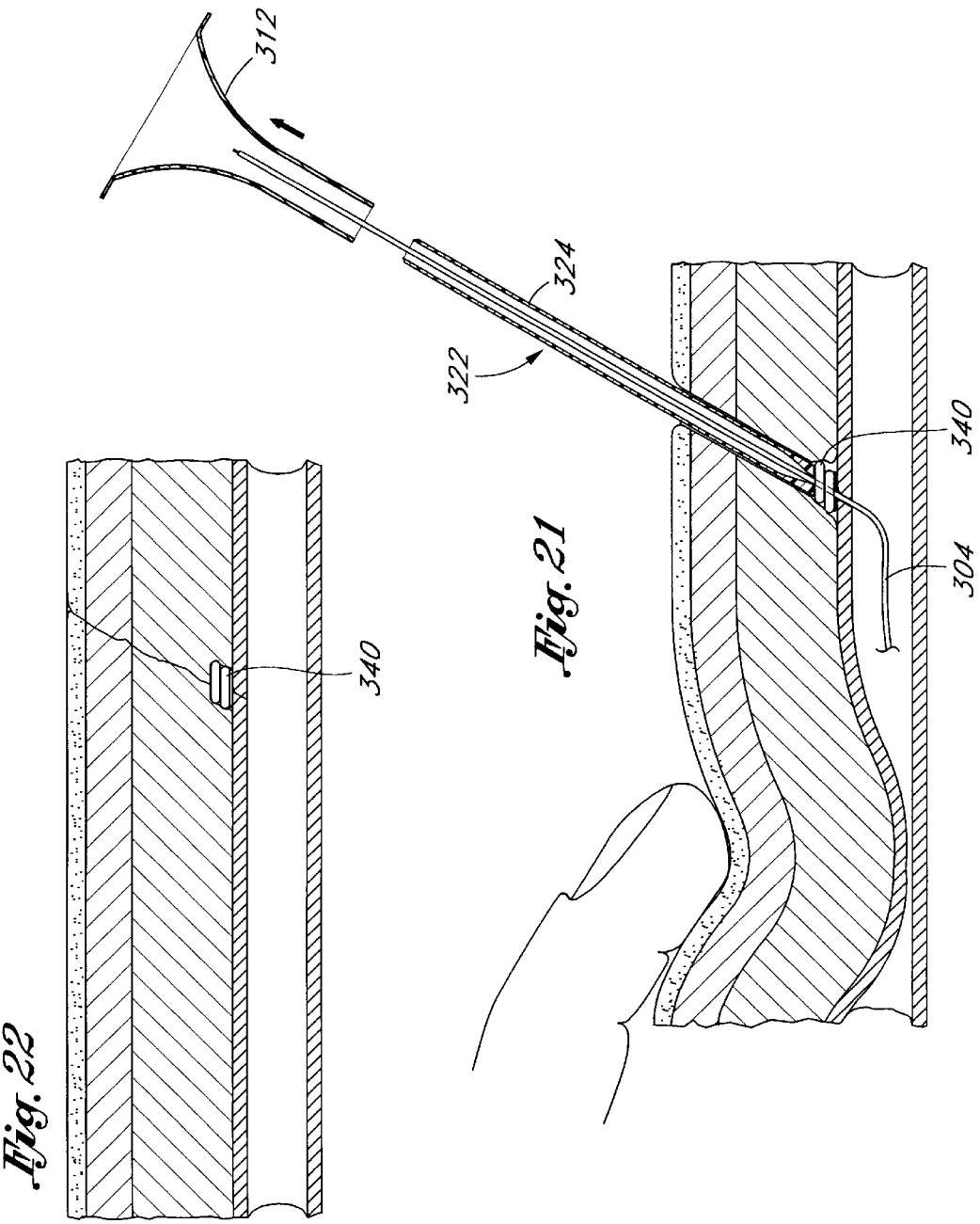

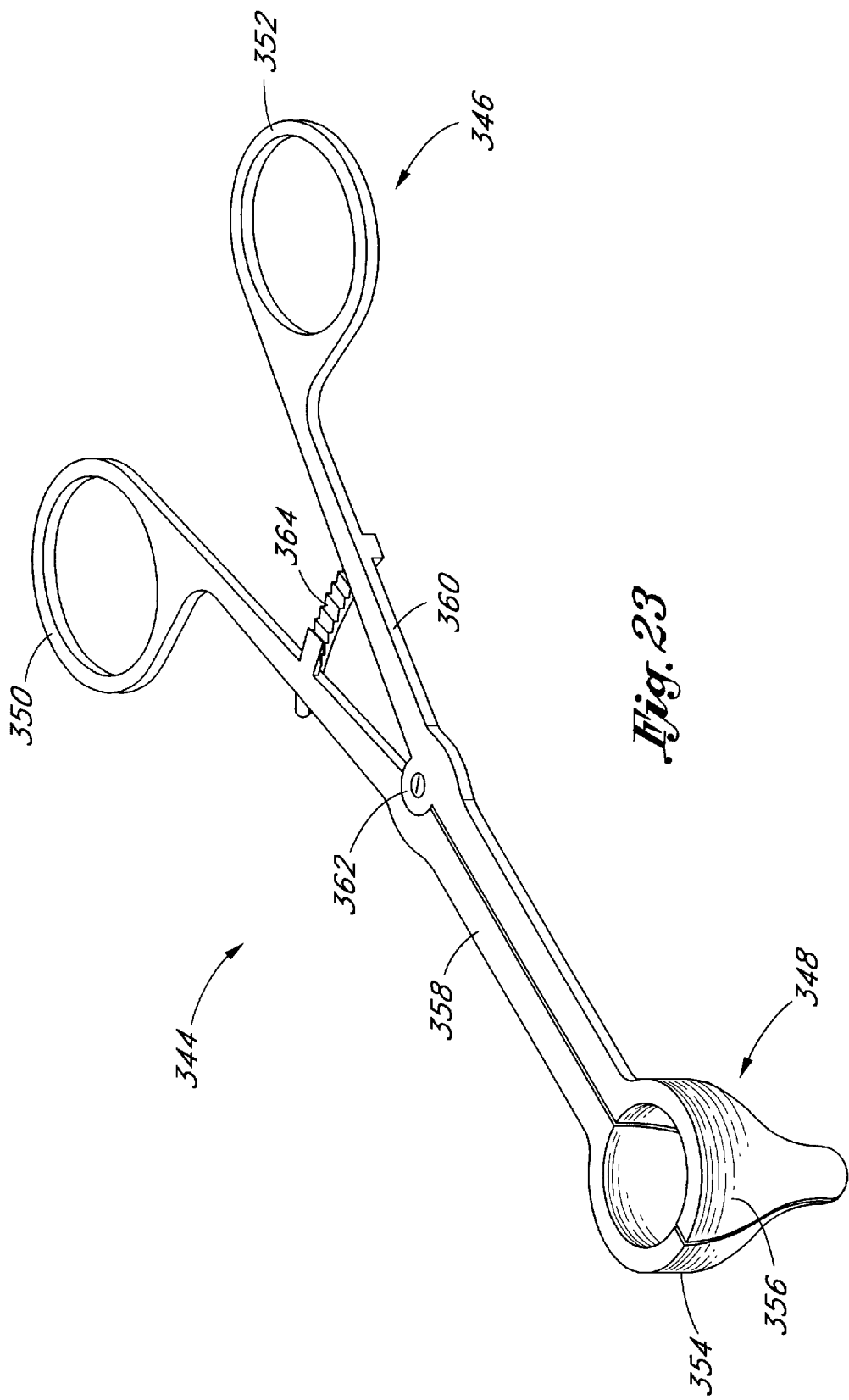

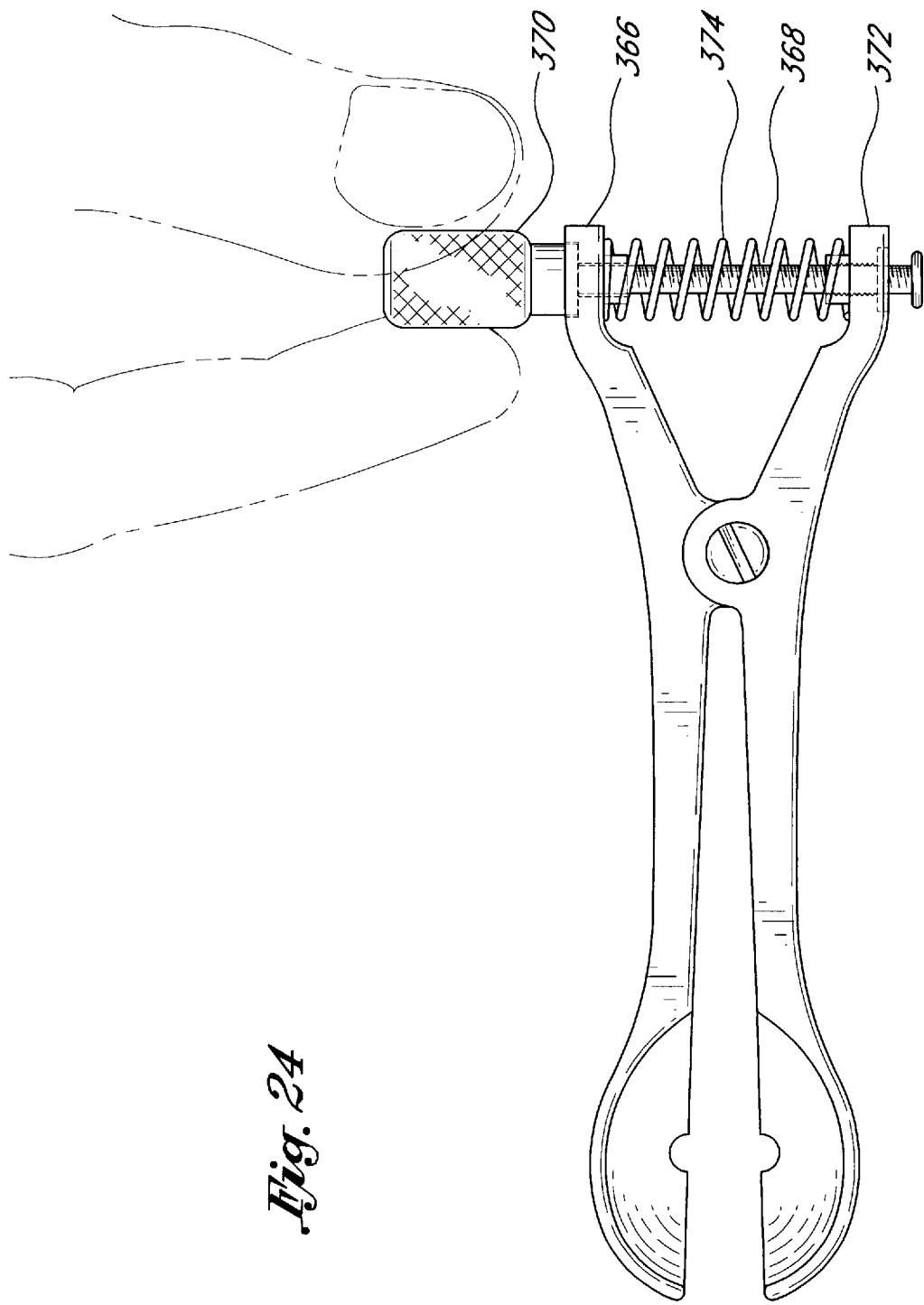

SURFACE OPENING ADHESIVE SEALER

RELATED CASE

This application is a continuation-in-part of application Ser. No. 08/314,049, filed Sep. 28, 1994 now U.S. Pat. No. 5,653,730 which is a continuation-in-part of Ser. No. 08/127,769, filed Sep. 28, 1993 now abandoned.

BACKGROUND OF THE INVENTION

1. Field of the Invention

This invention relates to a method and an associated device for sealing a puncture in a vessel within mammals. In particular, the invention relates to a method and an associated device for delivering a sealant patch and/or tissue adhesive to seal a puncture in a vessel.

2. Description of Related Art

Percutaneously accessing major vascular structures is a key step in a variety of diagnostic and therapeutic procedures, including Percutaneous Transluminal Coronary Angioplasty (PTCA), Percutaneous Coronary Angiography and Percutaneous Coronary Atherectomy. After the procedure is completed, the instruments used to perform the procedure are withdrawn from the vessel leaving a potential source of bleeding.

The most common method used to prevent post-procedure bleeding at the access site involves the application of direct pressure to the perforation site until normal physiologic pathways have sealed the access site. There are several problems with this method. First, the pressure application technique may fail to prevent hemorrhage. Such a hemorrhage may be life-threatening hemorrhage or lead to a large hematoma. A large hematoma in the groin, for instance, may compromise the major nerve supply to the anterior lower extremity.

Secondly, the pressure application technique extends the length of the in-hospital stay. For example, a PTCA may be completed in 2 to 3 hours, but the patient will typically be hospitalized for several additional hours or overnight, simply to allow the access site to seal physiologically. During this extended hospital stay the patient is required to stay immobile, often with a sand bag taped to his thigh (in the case of femoral artery access).

These complication are exacerbated where PTCA procedures are performed in elderly patients which commonly have arteries with reduced natural elasticity. The access perforation in a relatively inelastic artery does not contract or shrink upon itself to the same extent that would occur with an artery of normal elasticity. The resulting, undeflected perforation in a relatively inelastic artery typically is two to three times larger than an access perforation in a normal artery, further complicating the initiation of hemostasis and the normal physiologic sealing of the access site.

More than 500,000 PTCAs were performed worldwide in 1992 (Cowen Report, March 1993), as well as several times that number of other procedures requiring accessing major vascular structures percutaneously. Thus, the increased length of in-hospital stay necessitated by the pressure application technique considerably increases the expense of procedures requiring such vascular access.

A technique that would allow faster and safer sealing of a vascular access site would save a significant amount of health care resources. There remains a need for such a technique.

SUMMARY OF THE INVENTION

There is provided in accordance with one aspect of the present invention a method of sealing a vascular perforation. The method comprises the steps of providing a patient having a vascular perforation and a tubular access catheter extending through the perforation and into the vessel. The access catheter is proximally withdrawn until a distal end of the catheter is positioned inside the patient but outside of the perforation adjacent the vessel. A vascular patch is introduced into the proximal end of the access catheter, and the patch is advanced distally through the catheter. The patch is thereafter positioned against the vessel wall to seal the perforation.

Preferably, the method further comprises the step of monitoring blood pressure through the access catheter during the proximally withdrawing the access catheter step. The proximally withdrawing the access catheter step preferably is accomplished while monitoring blood pressure at the distal tip of the access catheter. An abrupt drop in blood pressure indicates that the distal end of the access catheter has been withdrawn through the perforation, and is positioned adjacent the outside wall of the vessel.

In accordance with a further aspect of the present invention, there is provided an alternate method of sealing a vascular perforation. The method comprises the steps of providing a patient having a vascular perforation and a guidewire extending therethrough. A bioabsorbable sealing tube having a central guidewire lumen extending therethrough is provided. The sealing tube is mounted coaxially on the guidewire, and advanced distally over the guidewire until a distal end of the sealing tube encounters resistance to further distal progress as a result of the vessel wall. Preferably, the sealing tube is gently pressed against the vessel wall for a sufficient period of time to seal the vascular perforation, and the guidewire is withdrawn from the patient.

In accordance with a further aspect of the present invention, there is provided a method of percutaneous transluminal coronary angioplasty or angiogram and inhibiting arterial bleeding at the arterial perforation site following the procedure. The method comprises the steps of perforating an artery to provide access to the arterial system, and advancing an introducer sheath through the perforation and into the artery.

An angioplasty catheter is introduced through the introducer sheath and into the artery. The catheter is advanced to a preselected treatment site and the site is treated with the catheter.

The catheter is thereafter withdrawn from the artery, and the introducer sheath is withdrawn from the perforation but left in position against the outside wall of the artery to provide access to the outside wall of the artery surrounding the perforation. A patch having a tissue adhesive thereon is thereafter advanced through the introducer sheath and placed against the wall to seal the perforation.

Further features and advantages of the present invention will become apparent from the detailed description of preferred embodiments which follow when considered together with the attached drawings and claims.

BRIEF DESCRIPTION OF THE DRAWINGS

FIG. 2 is a sectional side view of an applicator in accordance with another embodiment of the present invention;

FIG. 2a is a cross-sectional view of the applicator of FIG. 2 taken along lines 2a—2a;

FIG. 6a is a front elevational view of the applicator of FIG. 6 as seen in the direction of line 6a—6a;

FIG. 6b is a cross-sectional view of the applicator of FIG. 6 taken along the line 6b—6b;

FIG. 13 is a side elevational view of an expander cannula.

FIG. 14 is a left end view of the cannula of FIG. 13.

FIG. 15 is a side elevational view of an introducer cannula.

FIG. 16 is a bottom plan view of the introducer cannula of FIG. 15.

FIG. 17 is a schematic representation of an alternate embodiment of the present invention in position within a vessel.

FIG. 20 is a schematic representation as in FIG. 19, with the tissue expander removed and the patch applicator in position for attachment to the guidewire.

FIG. 20a is an exploded fragmentary view of the connection between the proximal end of the guidewire and the distal end of the patch applicator assembly.

FIG. 20b is an enlarged fragmentary view of the proximal end of the guidewire coupled to the distal end of the patch applicator.

FIG. 21 is a schematic view as in FIG. 20, with the patch applicator in position against the vessel wall and with the tissue speculum removed.

FIG. 22 is a schematic cross sectional representation of two vascular patches in position against a vessel wall.

FIG. 23 is a front perspective view of an adjustable tissue speculum in accordance with a further aspect of the present invention.

FIG. 24 is a top plan view of an alternate tissue speculum of the present invention.

DETAILED DESCRIPTION OF PREFERRED EMBODIMENTS

As discussed above, there is a need for a technique which will seal a vascular perforation created during a variety of commonly performed diagnostic and therapeutic procedures, including for example, Percutaneous Transluminal Coronary Angioplasty (PTCA), Percutaneous Coronary Angiography and Percutaneous Coronary Atherectomy. In addition, the device and method may have applications in the emergency treatment of trauma, wound closure following surgical procedures and the like. For convenience, the present disclosure will consider primarily the vascular perforation application.

An ideal technique would seal the perforation rapidly, cost effectively and permanently. If used to close a femoral or brachial artery, the technique should result in a seal that can withstand the uppermost potential limits of systolic blood pressure (around 300 mmHg) found in those vessels and the seal should be put in place with an absence of or no more than minimal enlargement of the original percutaneous entrance. One aspect of the present invention addresses the problems inherent in closing a perforation of a vessel, such as, for example, in a femoral or brachial artery following coronary artery or other vessel catheterization by providing a device, and a method that can be used to create a rapid and permanent seal.

Figure 1:
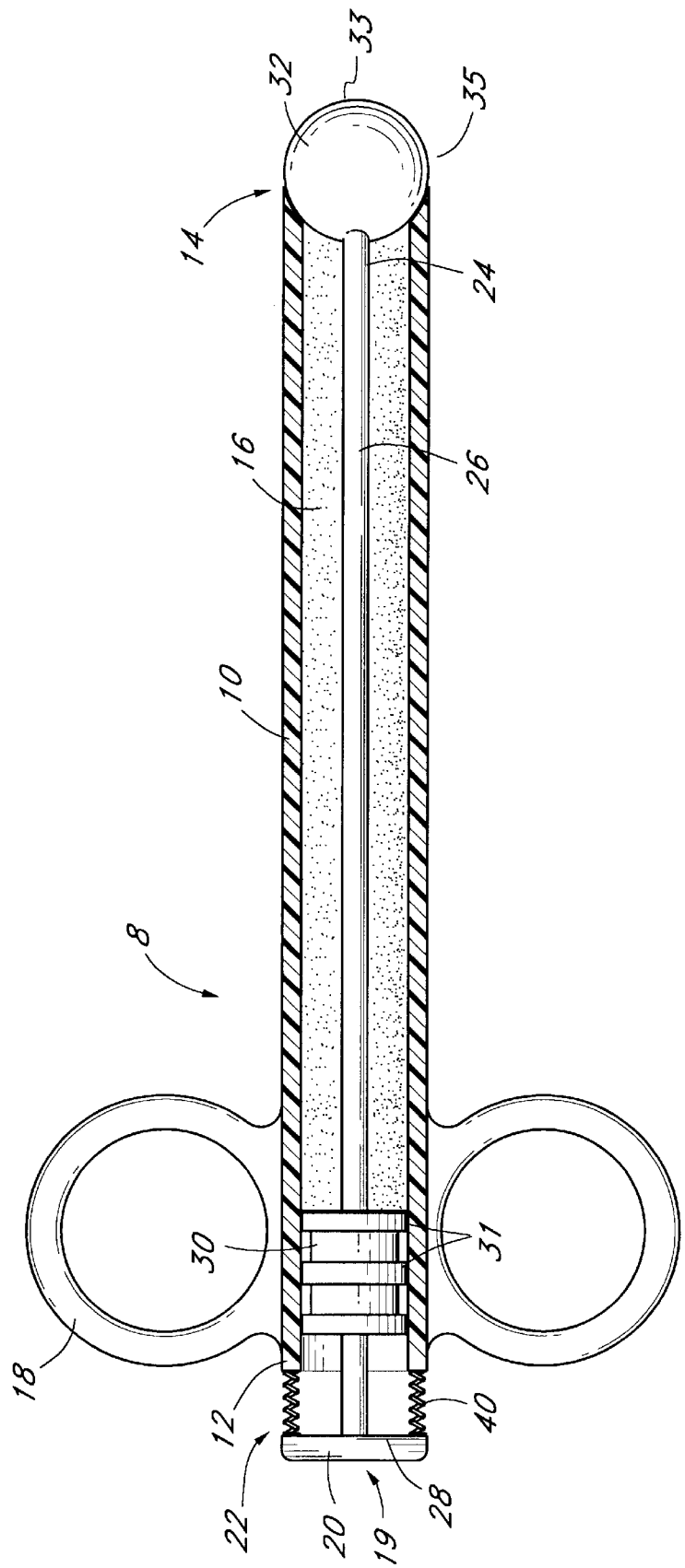
FIG. 1 is a sectional side view of an applicator in accordance with an embodiment of the present invention.

Referring to FIG. 1, there is illustrated one embodiment of the invention for delivering a tissue adhesive to a bodily surface. For convenience, tissue adhesive will be discussed herein, although any of a wide variety of other fluids or fluid-like media can be delivered utilizing the applicator of the present invention. The apparatus of the present invention can also be utilized to deliver materials to any of a wide variety of structures, as will be apparent to one of skill in the art. The present disclosure will discuss embodiments primarily intended for delivery to tissue of the type which covers or surrounds a lumen, cavity or organ, or potential lumen or cavity, within a human or other animal.

The illustrated embodiment comprises an applicator 8 having a generally tubular housing 10 with a proximal control end 12, a distal delivery end 14 and a reservoir 16. Located near the proximal control end 12 are gripping structures, such as a pair of rings 18 to improve the ease of grasping the applicator 8.

A control 19 is provided near proximal end 12 for controllably expressing adhesive from the reservoir 16, as will be discussed. Any of a variety of control structures can be used, such as push buttons, levers, plungers and the like. In addition, a control in the form of a rotating knob may be provided, that functions such that rotation of the knob causes a measured amount of adhesive to be released onto the delivery surface by opening a valve, or consecutively opening and closing a valve, leading from the reservoir. Tactile, auditory or visual feedback or a combination of feedback may be provided as part of the knob control to alert the operator when the measured amount of adhesive has been expressed. Other types of controls will be apparent to one of skill in the art in view of the disclosure herein.

The illustrated control 19 comprises a spring loaded proximal end 22, a distal end 24 and a shaft 26. The proximal end 22 comprises a movable button 20 having a stop 28 of such dimensions or structures that its axial distal travel is limited by the proximal end 12 of the tubular housing 10.

The permissible axial travel of moveable button 20 is determined by the desired volume of adhesive to be expressed upon depression of the button 20. Preferably, the applicator 8 of the present invention is provided in a single unit dose delivery form, so that a single depression of button 20 or a singe activation of another control to its limit causes a single unit volume of adhesive, which has been predetermined at the point of manufacture for an intended application, to be expressed from the distal end 14 of the applicator 8.

For example, in an embodiment of the applicator 8 for use following PTCA arterial perforations, a volume of generally no more than about 1.0 mm$^3$, and preferably no more than about 0.5 mm$^3$ of adhesive will desirably be delivered. Other structures for limiting the delivered volume can be readily incorporated into the applicator 8 by one of skill in the art.

The control 19 is preferably linked to a moveable wall 30 in the reservoir 16. Manipulation of the control 19 advances the moveable wall 30 in a manner that reduces the volume of the reservoir 16, thereby expressing the contents of the reservoir by way of an applicator 32, as discussed below. The moveable wall 30 may comprise a moveable diaphragm, other flexible wall, slidable piston, or other structure for expressing contents from reservoir 16 in response to manipulation of control 19. For instance, as illustrated in FIG. 1, the flexible wall 30 is a slidable piston or plunger with a plurality of annular seals 31 which prevent undesired proximal flow of adhesive from the reservoir 16.

In the illustrated embodiment, adhesive is expressed from the reservoir 16 by way of a valved opening 35 for providing valved fluid communication between the reservoir and the delivery surface 33. Conveniently, the same axial distal motion produced by depression of button 20 both displaces the moveable wall 30 and opens the valve 35 to permit expression of adhesive therethrough.

In this embodiment, the applicator 32 comprises a generally radially symmetrical structure, such as a sphere. The proximal portion of this sphere seats within or against the distal end 14 of tubular body 10, to enclose the reservoir 16 therein. Preferably, a biasing means, such as a spring 40, is provided for biasing the valve 35 in the closed position. Alternative biasing means can also be used, such as polymeric springs and structures which utilize the elastic deformation properties of a plastic material.

Depression of button 20 unseats the applicator 32 from the distal end 14 of housing 10, to provide an annular flow path around applicator 32. Adhesive expressed through valve 35 travels around the applicator 32 to coat a delivery surface 33 generally on the distal portion thereof.

The delivery surface 33 on the applicator 8 can take any of a variety of forms. Optimally, the delivery surface 33 facilitates the application of a substantially uniform coat or layer of adhesive over an area that is larger than the arterial perforation site. In general, forms of delivery surface 33 which reduce the risk of any traumatic injury to the tissue are preferred, such as spherical, or other rounded, blunt tips. A relatively flat distal delivery surface 33 can also be utilized, as will be apparent to one of skill in the art and as discussed below. Alternatively, delivery surface 33 comprises an absorptive blotter material, a permeable membrane or other microporous structure for permitting expression of adhesive directly therethrough.

In general, it is desired that the delivery surface 33 be sufficiently sized relative to the perforation of the vessel wall that the delivery surface 33 will not be penetrable through the perforation unless excessive distal force is applied. In a typical PTCA procedure, the natural elasticity of a major artery wall will normally cause the perforation 60 (FIG. 3) to shrink to about 30% of its original area, upon removal of the procedure instrumentation. This natural shrinkage leaves a vessel wall perforation approximately 1 mm in diameter for relatively elastic, healthy tissue. For the purposes of the present invention, therefore, an applicator 8 having a delivery surface 33 with an effective delivery diameter of at least about 2 mm and preferably a delivery surface of about 3 mm will be utilized.

With this structure, the operator can readily determine through tactile feedback when the delivery surface 33 is securely placed in contact with the vessel wall, yet the risk of perforation through the vessel wall is minimized. This reduces the likelihood that the delivery surface 33 will be introduced into the vessel, which could undesirably introduce adhesive into the bloodstream.

In addition to or as an alternative to reliance upon the size of the delivery surface 33 for limiting distal travel of the applicator 8, other structures, such as distally extending locating pins, radio opaque markers, and the like, can be incorporated into the applicator 8 of the present invention.

Figure 4:
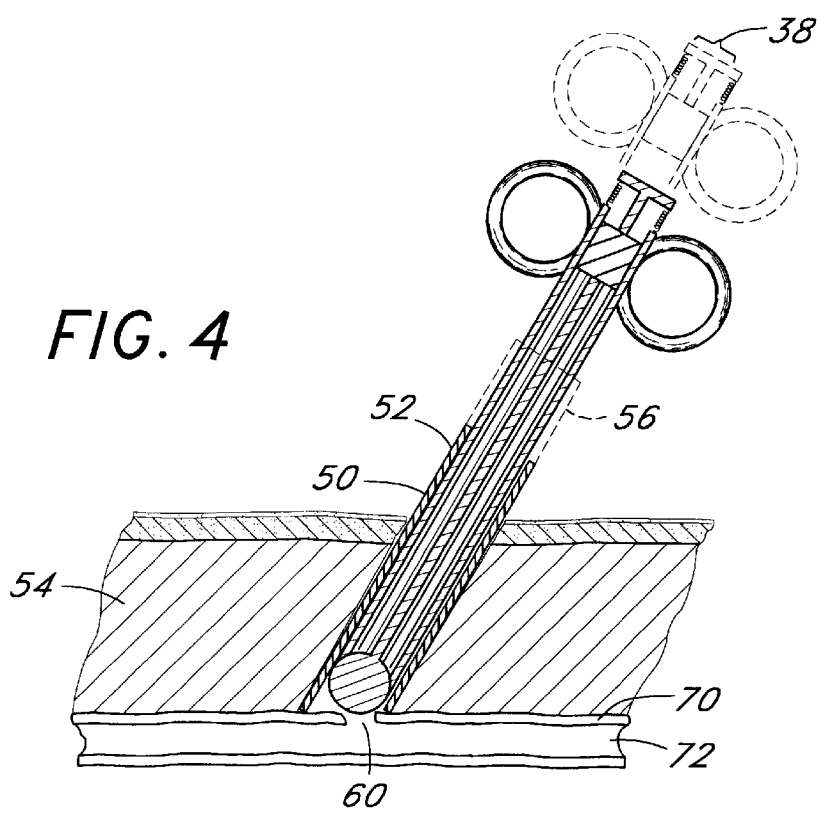

The distal end 14 of the applicator 8 is preferably configured in a manner that minimizes or prevents any contact between the delivery surface 33 and the tissue through which the delivery surface 33 must travel en route to the perforation 60 on the vessel wall. In one embodiment, this is accomplished by introducing the applicator 8 through a tubular introduction cannula 50, as is illustrated in FIG. 4 and will be described infra. In general, the cannula 50 has a sufficient interior diameter to accept the applicator 8, yet a sufficiently small exterior diameter to permit convenient penetration up to the perforated vessel wall.

Preferably, the distal end 54 of the cannula 50 exposes both the perforation 60 and a sufficient area of adjacent vessel wall surrounding the perforation 60 so that a sufficient volume of adhesive can be delivered from delivery surface 33 to the vessel wall. For a typical PTCA arterial perforation 60, having a diameter of about 1 mm, an introduction cannula 50 having an inside diameter of about 3 mm and an outside diameter of about 4 mm at its distal end 54 may conveniently be used.

Figure 3:
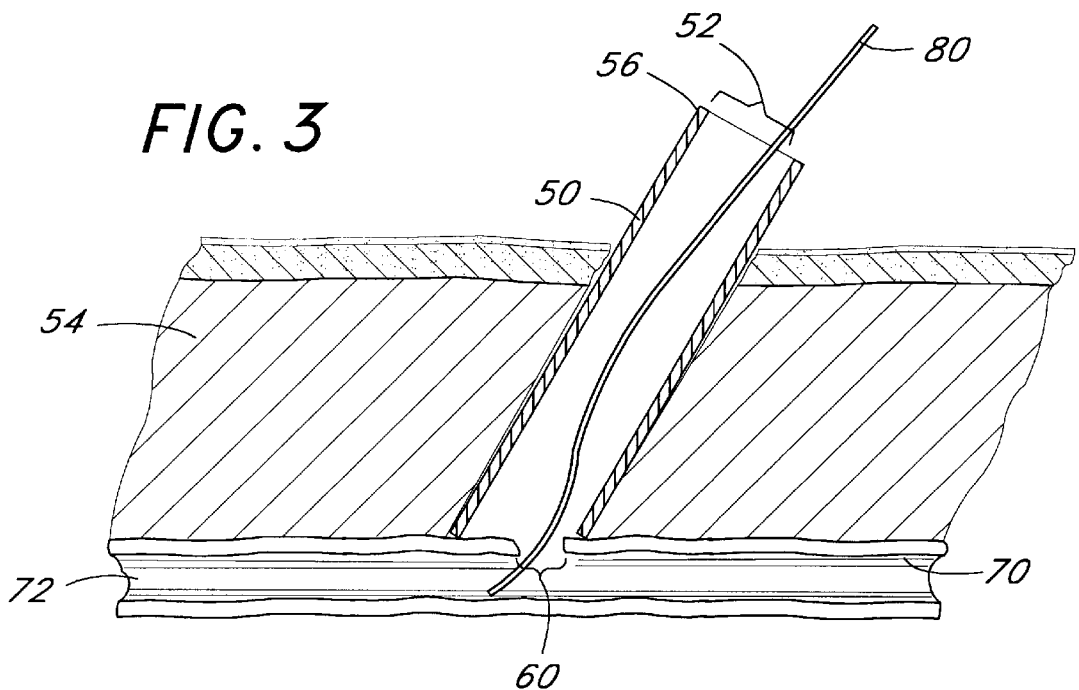
FIGS. 3 and 4 schematically illustrate a series of method steps involved with a preferred treatment method of the present invention.

Alternatively, the function of introduction cannula 50 can be readily accomplished by a structure integrally formed or secured to the applicator 8. For example, the delivery surface 33 can be retractably disposed within an outer tubular housing, as will be readily appreciated by one of skill in the art in view of the disclosure herein. As is illustrated in FIG. 3, the distal end of the cannula 50 or other introduction structure is preferably inclined in a manner that permits uniform contact to the vessel wall while the longitudinal axis of the applicator 8 is inclined at an angle to the vessel wall, which approximates the typical entry angle for the percutaneous perforation.

The reservoir 16 contains any of a variety of tissue adhesives. Suitable adhesives for in vivo use include adhesives within the cyanoacrylate family. In one preferred embodiment, the tissue adhesive comprises one or more of methyl cyanoacrylate, ethyl cyanoacrylate, n-propyl cyanoacrylate, isopropyl cyanoacrylate, n-butyl cyanoacrylate, isobutyl cyanoacrylate, n-amyl cyanoacrylate, isoamyl cyanoacrylate, 3-acetoxypropyl cyanoacrylate, 2-methoxypropyl cyanoacrylate, 3-chloropropyl cyanoacrylate, benzyl cyanoacrylate, phenyl cyanoacrylate, alkenyl cyanoacrylate, butyl-2-cyanoacrylate, alkoxyalkyl 2-cyanoacrylates or fluorinated 2-cyanoacrylates or combinations, thereof. More preferably, the tissue adhesive comprises ethyl cyanoacrylate or butyl-2-cyanoacrylate. These latter two compounds, available from Loctite Corporation (Hartford, Conn.), are normally in a liquid state with water-like viscosity. They harden almost instantaneously upon exposure to atmospheric humidity. Therefore, the reservoir 16 is provided with moisture-tight proximal and distal ends formed by the moveable wall 30 and the proximal end of the applicator 32, to maintain the tissue adhesive in liquid state prior to expression. Preferably, the device is also produced under low humidity conditions and stored in a desiccated package. A removable distal cap (not illustrated) may also be used.

Cyanoacrylate adhesives have been found to harden relatively rapidly when stored below a critical volume of adhesive. Hence, if cyanoacrylate is used, it will be preferable for the reservoir 16 to contain more adhesive than is necessary to seal a typical vascular access site. Preferably, a reservoir volume of at least about 1 to 2 gm is provided to maintain the cyanoacrylate in liquid form in the applicator prior to use. The total volume of adhesive, the desiccation measures and sealing structures on the reservoir 16 can be optimized to produce a desired shelf life by one of skill in the art in view of the disclosure herein.

When used to seal an in vivo tissue surface, cyanoacrylates have several particular advantages. First, they harden almost instantaneously on contact, because of the moisture content of most tissues. For example, they will harden when placed on living vascular walls, and endothelial and mesothelial surfaces. Second, experiments by the inventor indicate that cyanoacrylate sealed vascular punctures can withstand several times the maximum potential systolic pressure, and hence, would not be expected to fail when used to seal a perforation on a vascular wall. Also, cyanoacrylates are naturally thrombogenic. This is an advantage in sealing vascular walls as it promotes the first step in healing the wall. Further, because it seals so rapidly, the risk of embolization or migration can be minimized through the use of the applicators disclosed herein.

Various compounds may be added to the cyanoacrylates to alter the properties of the adhesive. For example, polyacrylic acid having a molecular weight of 200,000 to 600,000 may be cross-linked to the cyanoacrylate to form a suitable biocompatible material. These combination compounds allow the absorbability and resorption rate to be coordinated with the tissue regeneration rate and feature higher elasticity than cyanoacrylates alone. Other additives, such as stabilizers, viscosity modifiers and medications can also be included as desired.

Figures 2, 2A:
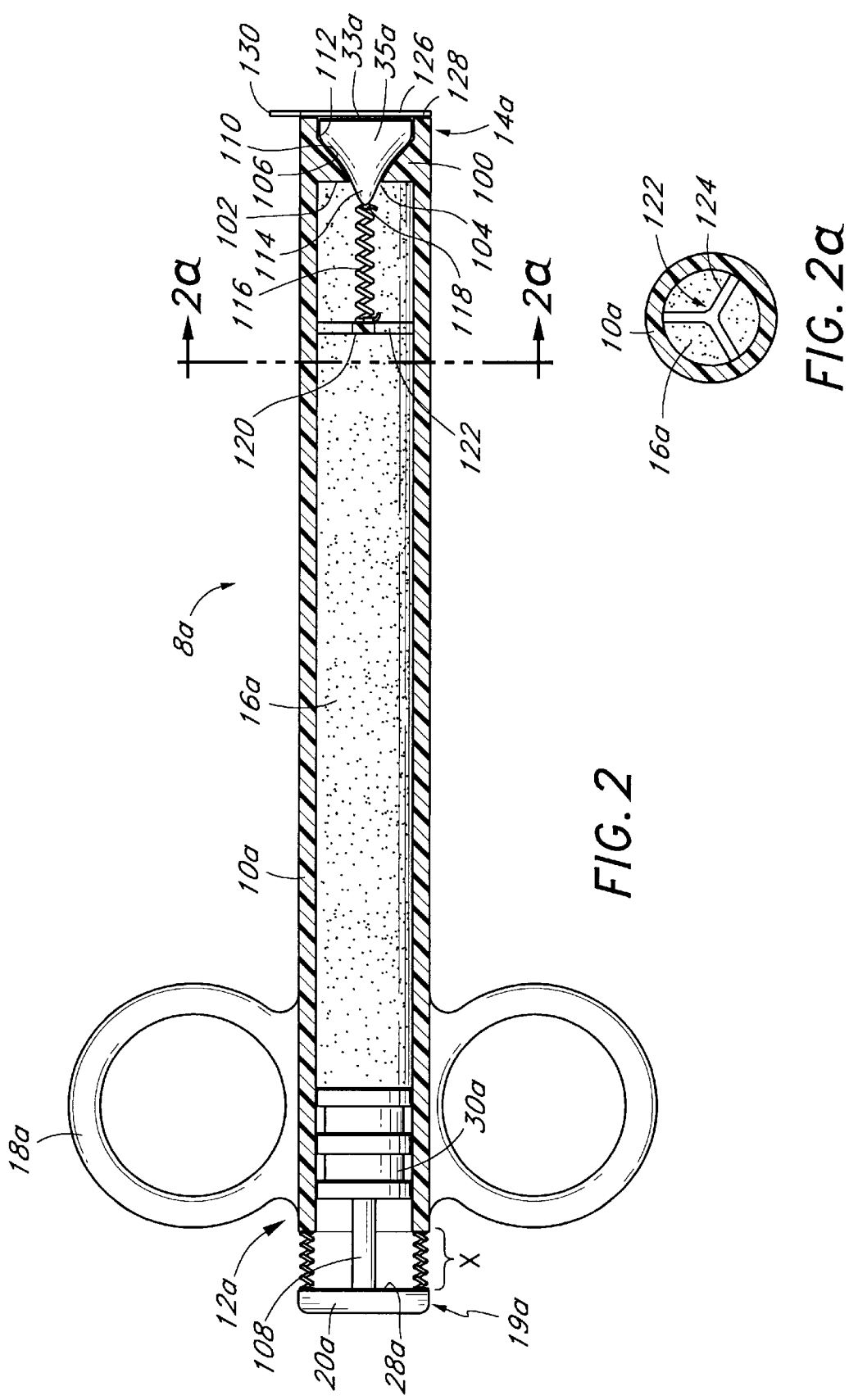

FIG. 2 illustrates another embodiment of the invention for delivering a tissue adhesive to a body surface. For ease of understanding, like reference numerals with an "a" suffix have been used to designate similar elements between the two embodiments.

The applicator 8a has a generally tubular housing 10a with a proximal control end 12a, a distal delivery end 14a and a reservoir 16a. The reservoir 16a desirably contains a tissue adhesive, and preferably contains any of the variety of tissue adhesives described above. As noted above, the reservoir 16a desirably contains more tissue adhesive than is necessary to seal a typical vascular access site in order to maintain the tissue adhesive in a liquid form. It is also contemplated, as noted above, that the reservoir 16a could contain any of a wide variety of other fluids or fluid-like media as well.

The applicator 8a may include grasping structure to ease handling and manipulating the applicator 8a. For this purpose, in the illustrated embodiment, the applicator 8a includes a pair of rings 18a located near the proximal control end 12a of the applicator 8a.

The distal delivery end 14a of the applicator 8a defines an annular valve seat 100 which cooperates with a valve 35a. The valve seat 100 includes a proximal wall 102 which defines an aperture 104 that opens into the reservoir 16a. The aperture 104 has a diameter smaller than that of the reservoir 16a as defined by the tubular housing 10a. The valve seat 100 also includes a sealing surface 106 which preferably tapers, radially outwardly in the distal direction, from the aperture 104 towards the wall of the tubular housing 10a. The surface 106 thus defines generally a frusto-conical shape which mates with a correspondingly shaped surface of the valve 35a, as discussed below. The valve seat 100 also is configured to receive the valve 35a to a sufficient extent that an applicator surface 33a of the valve 35a lies generally flush with or slightly proximally of the distal delivery end 14a of the applicator 8a when the valve 35a is closed (i.e., is seated against the valve seat 100).

As seen in FIG. 2, the applicator 8a also includes a control 19a which controls the expression of adhesive from the reservoir 16a. The control 19a is positioned at the proximal end 12a of the applicator 8a. As with the above-described embodiment, any of a variety of control structures can be used, such as, for example, push buttons, levers, plungers, rotatable knobs, and the like. In the illustrated embodiment, the control 19a includes a plunger 30a disposed within the reservoir 16a. A movable button 20a, attached to the plunger 30a by a stem 108, is provided for actuating movement of the plunger 30a within the reservoir 16a.

A distance X between the proximal end 12a of the tubular housing 10a and a distal surface 28a of the button 20a determines the permissible amount of axial travel of the button 20a and plunger 30a, and hence defines the desired volume of adhesive to be expressed upon depression of the button 20a.

Like the above-described applicator 8 of FIG. 1, the present applicator 8a desirable delivers a single dose of tissue adhesive. The delivered volume of tissue adhesive desirably is predetermined at the point of manufacture for an intended application. It is contemplated that those skilled in the art will really appreciate that any of a variety of volumes of adhesive may be expressed depending upon the particular surgical application.

The valve 35a, disposed at the distal delivery end 14a of the applicator 8a, generally has a conical configuration. The distal end of the valve 35a includes an a traumatic application surface 33a which transitions into a valve surface 110 of the valve 35a by a rounded shoulder region 112. The valve surface 110 of the valve 35a has a generally frusto-conical shape which is sized and configured to mate with the valve seat 100 at the distal end 14a of the tubular housing 10a so as to seal closed the reservoir 16a.

The valve 35a desirably is normally closed. That is, the valve 35a desirably is biased against the valve seat 100. Any of a variety of biasing structures can be used, such as, for example, springs, diaphragms, magnets, and the like. In the illustrated embodiment, a helical spring 116 biases the valve 35a in the proximal direction against the valve seat 100.

In one embodiment, a distal end 118 of the spring 116 passes through a transverse aperture of the valve proximal end 114. The spring 116, however, may be attached to the valve 35a by any of a variety of other means known in the art as well.

The tubular housing 10a includes structure which supports a proximal end 120 of the spring 116. In the illustrated embodiment, the tubular housing 10a includes a spider structure 122 which extends within the tubular housing 10a. As best illustrated in FIG. 2a, the spider structure 122 includes a plurality of legs 124, preferably three legs, which extend from the wall of the housing 10a to the center of the reservoir 16a. The proximal end 120 of the spring 116 is attached to the spider structure 122 in a conventional manner. Alternatively, proximal end 120 of spring 116 is secured directly to the inner surface of the housing 10a.

Activation of the control 19a advances the plunger 30a in the distal direction to compress the adhesive within the reservoir 16a. Once the produced pressure within the reservoir exceeds the biasing force acting on the valve 35a, the valve 35a opens to express adhesive onto the delivery surface 33a.

The delivery surface 33a desirably extends near or beyond the distal delivery end 14a of the housing 10a with the valve 35a opened. In this manner, the delivery surface 33a is positioned to contact the vascular wall surrounding the arterial perforation site. Additionally, the generally blunt configuration of the delivery surface 33a with rounded edges 112 reduces the risk of any traumatic injury to the tissue as well as prevents unintentional penetration or advancement into the vessel, as discussed above.

With reference to FIG. 2, the applicator 8a may also include a release layer 126 which covers the distal delivery end 14a of the tubular housing 10a and the distal delivery surface 33a of the valve 35a. The release layer 126 desirably adheres to the annular distal end surface 128 of the tubular housing 10a and not to the delivery surface 33a. The release layer preferably includes a tab 130 to facilitate removal of the release layer 126 from the applicator 8a. In one embodiment, a small space is provided between the delivery surface 33a and the release layer 126 to permit coating the delivery surface 33a with adhesive prior to removal of the release layer 126. Preferably, the release layer is a transparent polymeric film such as teflon or polyethylene.

In another aspect of the present invention, there is provided a method for delivering a tissue adhesive to a surface which covers or surrounds a lumen, cavity or organ, or potential lumen or cavity, within a human or animal. In one preferred embodiment, the method comprises the steps of providing an applicator having an a traumatic delivery surface, a reservoir and a control for expressing media from the reservoir to the delivery surface.

The delivery surface is placed near or in contact with the tissue surface surrounding an opening therein, and the control is activated to express tissue adhesive from the reservoir to the delivery surface. The delivery surface is thereafter brought into contact or maintained in contact with the vessel wall to deliver a layer of adhesive to the vessel wall. These basic steps are discussed in greater detail below.

This method can be used to close any exposed surface which can be reached by the applicators 8, 8a described above. For example, it has uses in open laparotomy for closing the peritoneal surfaces of the various hollow viscera, diaphragm and omentum. It has potential in sealing the surface of liver and spleen to prevent intraperitoneal hemorrhages. Further, it can be used to seal lung, heart and pleura, as after traumatic, iatrogenic or disease induced perforation.

In another aspect of the present invention, a method is provided for inhibiting arterial bleeding at the arterial access site after Percutaneous Transluminal Coronary Angioplasty (PTCA), Percutaneous Coronary Angiography, Percutaneous Coronary Atherectomy and similar procedures. In this method, access into an artery such as the femoral or brachial is made percutaneously in a manner well known to those with skill in the art. At the conclusion of the procedure, the catheter is withdrawn and pressure applied proximal to the access site to inhibit bleeding. The applicator 8 or 8a, as described above, is advanced through the skin entrance site until the delivery end 14 contacts the vascular perforation 60 and a portion surrounding vascular wall 70. Tissue adhesive is expressed from the delivery end 14 of the applicator 8 and allowed to harden over the perforated tissue, sealing the opening. The applicator 8 is withdrawn and the skin entrance dressed in a usual manner.

Another preferred embodiment of a method for inhibiting arterial bleeding at the arterial access site after catheterization comprises the additional step of positioning the cannula 50 over vascularly indwelling instrumentation, as described below. Before describing this method, a summary of a representative intravascular surgical procedure utilizing a percutaneous opening will be given to further understanding of the invention.

In a representative procedure, an introduction needle is inserted percutaneously into a vascular structure, for example, the femoral artery. A guidewire is passed through the introduction needle to a desired site and the needle is withdrawn leaving the guidewire in position. Next, first and second sheaths, usually an introducer sheath and a dilator sheath, are passed over the guidewire and inserted into the vascular structure. The guidewire and first sheath are removed leaving the second sheath in place. Then the catheter or other instrumentation is inserted through the second sheath and threaded to a desired location, such as an atherosclerotic plaque.

Once the intravascular procedure has been completed, the catheter is removed. The usual method of hemostasis involves also removing the second sheath and applying pressure to the perforation site through the skin until hemostasis has occurred. However, an obturator may be inserted into the second sheath and both obturator and second sheath left in place for a period of time, prior to their removal. This additional step depends on the type of procedure and the patient's state of coagulation among other variables.

Referring now to FIGS. 3 and 4, one application of the present invention is illustrated. A cannula 50, of the present invention, has a proximal end 52, a distal end 54 and a minimum inner dimension 56 greater than the maximum dimension of the perforation 60. Further, the cannula 50 has a minimum inner dimension 56, at the proximal end 52 at least, that is greater than the maximum external dimension 38 of the tubular housing 10. This feature allows the applicator to axially movably fit within the cannula 50.

The cannula 50 may have a smaller outer dimension (not shown) at the distal end 54 than at the proximal end 52 to facilitate placement of the catheter through the skin tract. In this latter embodiment, the inner dimension of the distal end is still large enough to allow the delivery surface 33 of the applicator 8 to contact the portion of the vascular wall 70 surrounding the perforation. The cannula 50 alternatively is provided with a larger internal dimension at its distal end to expose a relatively larger area of vascular surface surrounding the perforation site.

After completing the intravascular surgical procedure, the catheter (not shown) is withdrawn. A guidewire, 80 is placed through the second sheath (not shown) and the second sheath is withdrawn. External pressure is applied proximal (upstream) to the perforation as needed to control bleeding.

The cannula 50 is inserted over the guidewire 80 until the operator obtains tactile feedback that the cannula 50 has contracted the vascular wall 70. FIG. 3 illustrates the placement of the cannula 50 over the guidewire at the point where the cannula contacts the portion of the vascular wall 70 surrounding the perforation.

The guidewire 80 is removed leaving the cannula 50 in position over the perforation 60. Next, the applicator 8 is inserted through the cannula 50 and advanced distally until the delivery surface 33 contacts the vascular wall 70, without penetrating the perforation 60 into the vessel lumen 72. Again the operator will receive tactile feedback indicating that the delivery surface 33 has contacted the vascular wall 70. This step is shown in FIG. 4. Finally, an aliquot of tissue adhesive is expressed from the distal end 33 of the applicator 8, sealing the perforation 60. Both cannula 50 and applicator 8 are withdrawn from the body and a suitable dressing applied. Alternately, the cannula 50 can be withdrawn prior to discharging an aliquot of tissue adhesive.

Cyanoacrylate tissue adhesives will harden virtually on contact, and create a permanent seal. The operator may prefer to express tissue adhesive while the delivery surface 33 is spaced slightly apart from the tissue to be sealed. This permits the adhesive to flow over the delivery surface 33 and produce a relatively uniform coating for application to the target tissue.

Other embodiments will be readily apparent to those with skill in the art. For example, in addition to the above embodiment, the cannula 50 could be introduced over the catheter directly in procedures where the second sheath is withdrawn prior to the catheter. In another embodiment, a guidewire 80 is inserted prior to the withdrawal of the catheter, either through the catheter or between the catheter and the second sheath. The catheter and second sheath would be withdrawn leaving the guidewire and the cannula 50 would be placed as described above. In still another embodiment, the cannula 50 could be introduced over the second sheath rather than through the second sheath.

In yet another embodiment, the guidewire 80 is inserted into the perforation at the conclusion of the procedure. The instrumentation, other than the guidewire 80, is removed. An applicator with a central axially extending guidewire lumen (not illustrated) may then be threaded directly over the guidewire 80 until the distal end of the applicator contacts the portion of the vessel wall surrounding the perforation. The guidewire 80 is then removed and tissue adhesive is controllably expressed to seal the perforation. Finally, the applicator is removed and a suitable dressing applied.

In all cases, bleeding from the perforation site is preferably controlled by applying external pressure proximal (upstream) to the perforation. As described above, the natural elasticity of the vessel wall will normally cause the perforation to shrink, assisting in hemostasis.

Tissue adhesives of the type described above are well suited to seal a typical PTCA arterial perforation, which commonly has a non-dilated diameter of about 1 mm, where the arterial wall is relatively elastic. However, where the arterial wall is relatively inelastic, and the typical PTCA arterial perforation commonly has a non-dilated diameter of about 2–3 mm, it has been found desirable to use a porous patch 150 in combination with the tissue adhesive to further improve the integrity of the seal across the arterial perforation.

Figure 5:
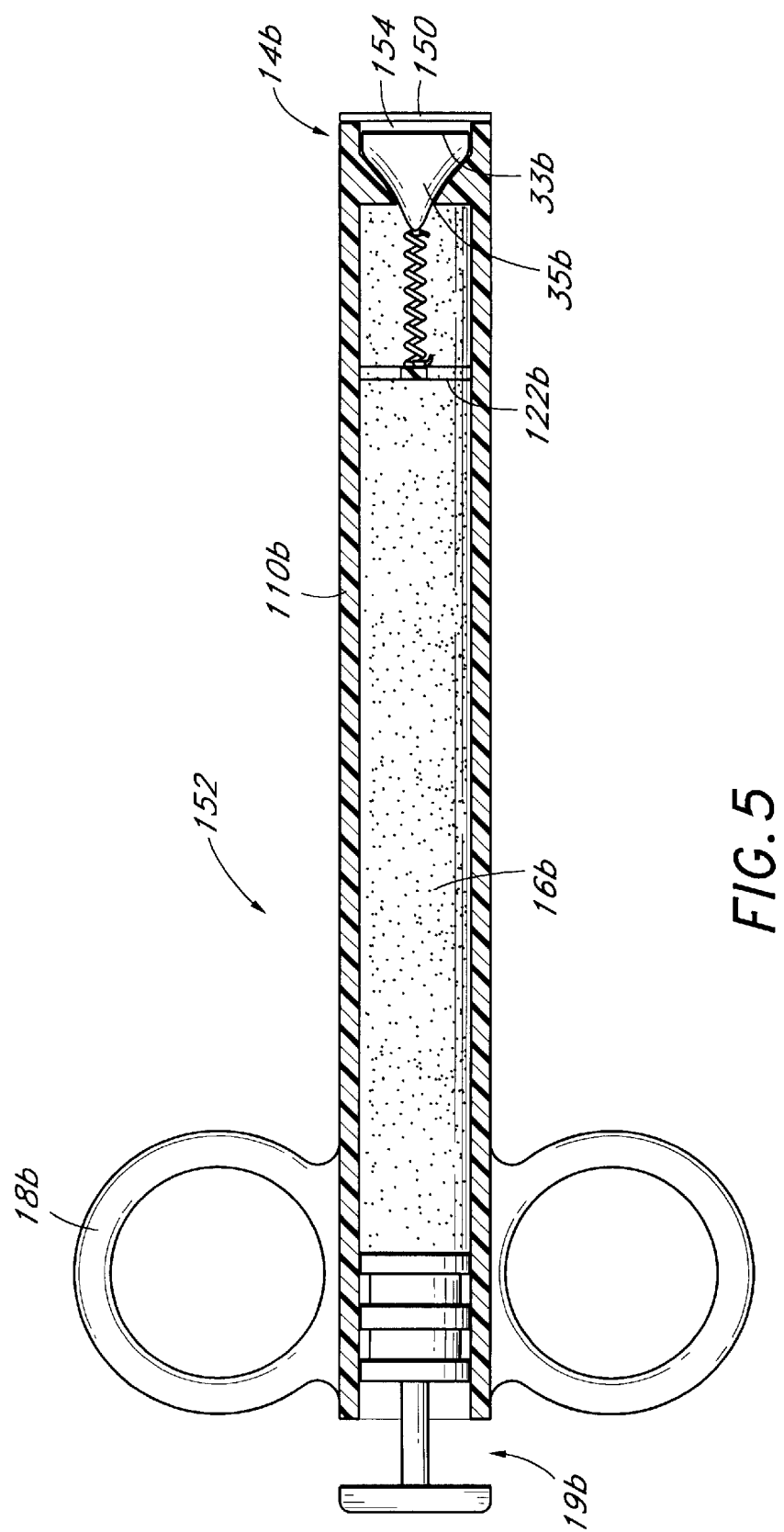
FIG. 5 is a sectional side view of an applicator in accordance with an additional embodiment of the present invention.

Thus, referring to FIG. 5, there has been provided in accordance with another aspect of the present invention an adhesive patch 150 used to seal a perforation in a vessel wall, and, more preferably, to seal a vascular perforation created during any of a variety of commonly performed diagnostic or therapeutic procedures.

The patch 150 desirably has a size larger than the perforation of the vessel (e.g., an artery) and may have any of a variety of shapes depending upon the application of the patch 150. In an illustrated embodiment, the patch 150 generally has a circular shape of a sufficient diameter to completely cover the perforation. It is understood, however, that the size of the patch 150 may only cover a portion of the perforation, yet extend across the perforation so as to attach to the surfaces of the vessel on either side of the perforation. The patch 150 preferably has a diameter of at last about 2 mm and preferably at least about 4 mm for application with a PTCA arterial perforation formed in an inelastic artery.

The patch 150 advantageously is porous so tissue adhesive can flow through the pores of the patch 150 to attach the patch 150 to the ablumenal surface adjacent the perforation and to seal the portion of the patch 150 extending across the perforation. In an exemplary embodiment, the pores have a size of about 300 microns, although it is understood that the pores could have a size ranging between $100\,\mu$ to $500\,\mu$, and more preferably ranging between $200\,\mu$ to $400\,\mu$.

The patch 150 is preferably formed of a mesh, weave or knitted material which is biocompatible, and preferably is biodegradable (i.e., is absorbable within the body). The patch 150 can be formed of any of a wide variety of suitable materials, such as, for example, polytetrafluoroethylene (PTFE), oxidized regenerated cellulose, Gelfilm™ available from the Upjohn Co. and collagen. A suitable material from which to form the patch 150 is a sterile absorbable mesh material (either knitted or woven) available commercially as VICRYL™ from Ethicon (a Johnson and Johnson company) of Somerville, N.J.

The patch 150 may be impregnated, coated, or otherwise pretreated at the point of manufacture with a tissue adhesive, such as, for example, any of the tissue adhesive types described above. In this manner, the adhesive coated surface of the patch 150 will adhere to the surface of the vessel surrounding the perforation upon application of the patch 150. Alternatively, the patch 150 and the tissue adhesive can be provided separately, and the patch 150 is saturated or coated with tissue adhesive at the time of application or just before application, as discussed below.

The patch 150 can be used to seal a puncture site in a viscera or vascular structure by applying the patch 150 and adhesive to the surface of the walls surrounding the perforation to seal the viscera or vascular structure. In order to apply the patch 150 and adhesive over the puncture site, it is desirable to use an applicator which has an a traumatic delivery surface to deliver the adhesive and the patch 150 to the perforation site.

Thus, in accordance with another aspect of the present invention, there is provided an applicator 152 to both deliver adhesive and apply the patch 150 to the perforation site. FIG. 5 illustrates an embodiment of applicator 152 in accordance with a preferred embodiment of the present invention. The applicator depicted by FIG. 5 is substantially identical to that illustrated in FIGS. 2 and 2a and described above. Accordingly, unless indicated otherwise, the above description of the applicator of FIG. 2 will apply equally to FIG. 5, and like reference numerals with a "b" suffix will be used for ease of understanding.

With reference to FIG. 5, the distal delivery end 14b of the tubular housing lob desirably extends slightly beyond the delivery surface 33b of the valve 35b. The distal delivery end 14b of the tubular housing 10b supports a patch 150. The patch 150 is constructed in accordance with the above description.

The patch 150 also includes on its proximal side around its peripheral edge a light coating of a releasable adhesive, which removably holds the patch 150 on the distal end 14b of the applicator 152 before application. The net release force required to pull the patch 150 from the adhesive should be low enough to permit the patch 150 to adhere to the vascular wall while permitting the applicator 152 to be separated from the patch 150. This can be accomplished in a variety of ways which will be readily apparent to one of skill in the art, including, for example, appropriate adhesive selection, and optimizing the surface area coverage of the adhesive.

The housing 10b defines a space between the patch 150 and the delivery surface 33b of the valve 35b. The space 154 has a sufficient size to allow adhesive expressed through the valve 35b to uniformly coat the patch 150 before application at the perforation site. In an exemplary embodiment, the space 154 has an axial depth ranging between 0.02 and 0.5 mm, and more preferably equal to about 0.1 mm.

A cap (not shown) can cover the distal end of the applicator 152 to protect the patch 150 and to maintain its sterility before application.

Distal movement of the control button 19b causes the valve 35b to open and express adhesive between the distal delivery surface 33b of the valve 35b and the patch 150. Adhesive permeates through the patch 150 to a point of saturation and expresses onto the distal side (i.e., the ablumenal surface) of the patch 150. As discussed more fully below, the patch 150 is thereafter applied over the perforation site. The tissue adhesive will harden virtually on contact to secure the patch 150 over the perforation and to seal the patch 150. The applicator 152 may thereafter be retracted proximally, breaking the connection between the applicator 152 and the patch 150.

Figure 6:
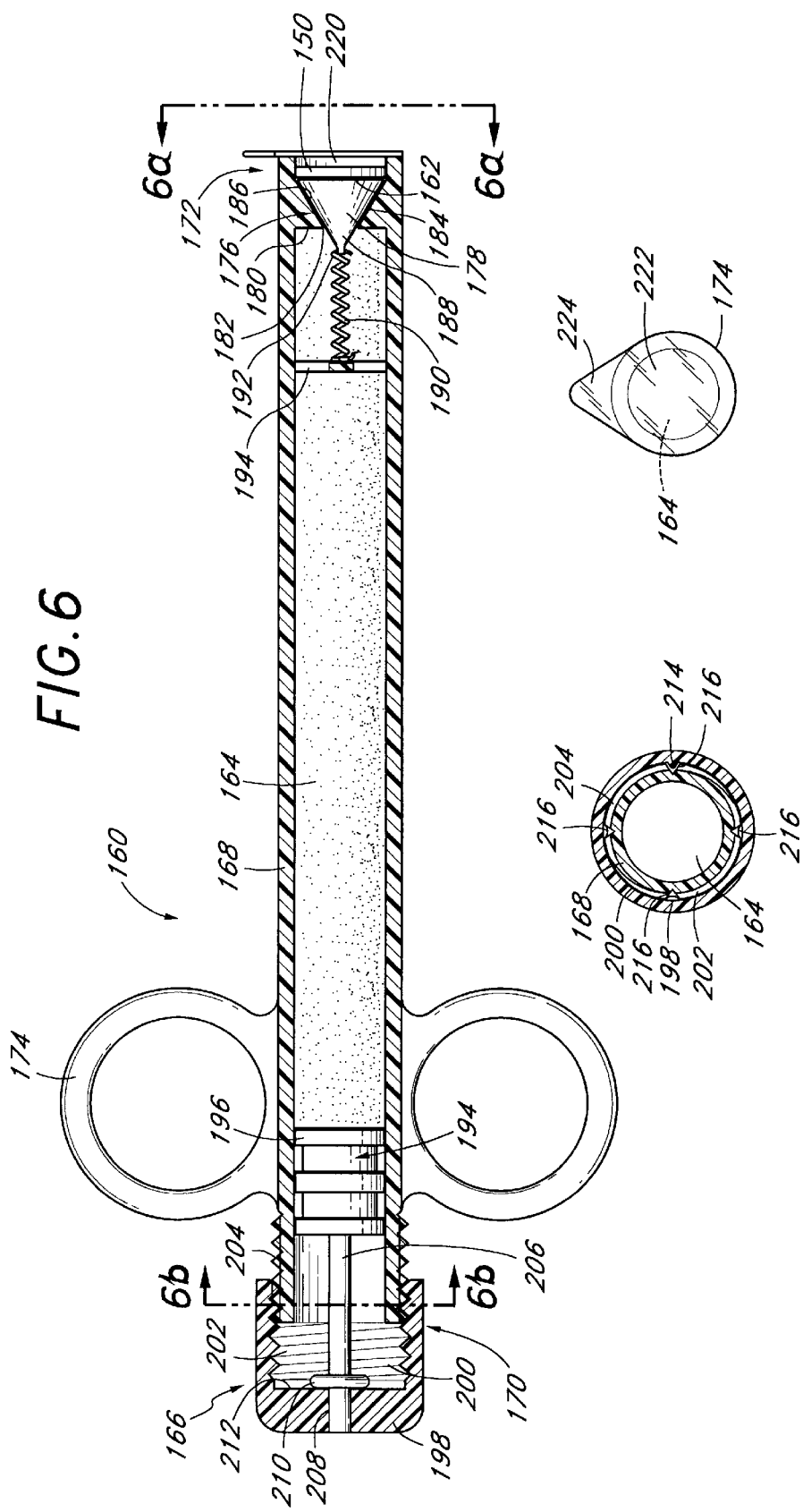
FIG. 6 is a sectional side view of an applicator in accordance with another embodiment of the present invention.

FIG. 6 illustrates another preferred embodiment of an applicator 160 for applying the sealant patch 150, which includes an atraumatic delivery surface 162, a reservoir 164 and a control 166 for expressing media from the reservoir 164 to the delivery surface 162 and the patch 150.

Like the above-described applicators, the present applicator 160 has a generally tubular housing 168 with a proximal end 170 and a distal end 172. The tubular housing 168 defines the reservoir 164. The reservoir 164 desirably contains a tissue adhesive, and preferably contains any of the variety of tissue adhesives described above. It is also contemplated, as noted above, that the reservoir 164 could contain any of a wide variety of other fluids or fluid-like media as well.

Like the above-described applicators, the present applicator 160 desirable delivers a single dose of tissue adhesive. The delivered volume of tissue adhesive desirably is predetermined at the point of manufacture for an intended application. It is contemplated that those skilled in the art will really appreciate that a variety of volumetric sizes of adhesive may be expressed depending upon the particular surgical application. In addition, as noted above, the reservoir 164 desirably contains more tissue adhesive than is necessary to seal a typical vascular access site in order to maintain the tissue adhesive in a liquid form for a suitable product shelf life.

The applicator 160 can also include grasping structures to ease handling and manipulating the applicator 160. For this purpose, in the illustrated embodiment, the applicator 160 includes a pair of rings 174 located near the proximal end 170 of the applicator 160.

The distal end 172 of the applicator 160 defines an annular valve seat 176 which cooperates with a valve 178. As with prior embodiments, the valve seat is conveniently formed by a radially inwardly extending annular ridge. The illustrated valve seat 176 includes a proximal wall 180 which defines an aperture 182 that opens into the reservoir 164. The aperture 182 has a diameter smaller than that of the reservoir 164 as defined by the inner surface of the tubular housing 168.

The valve seat 180 also includes a generally smooth sealing surface 184 which tapers radially outwardly in the distal direction, from the aperture 182 toward the wall of the tubular housing 168. The surface 184 defines generally a frusto-conical shape which mates with a corresponding surface of the valve 178, as discussed below. The valve seat 176 also is configured to receive the valve 178 such that the delivery surface 162 of the valve 178 lies within the tubular housing 168 when the valve 178 is closed (i.e., is seated against the valve seat 176).

The valve 178, disposed at the distal end 172 of the applicator 160, generally has a conical configuration. The distal end of the valve 178 includes the flat or slightly convex delivery surface 162. The valve 178 also includes a generally smooth valve surface 186 which is sized and configured to mate with the corresponding surface of the valve seat 176 so as to seal closed the reservoir. The valve 178 also includes a proximal tip 188 which is provided with a transverse aperture (not shown) for attachment to the spring.

As with the above embodiments, the valve desirably is normally closed, biased against the valve seat 176. Again, any of a variety of biasing structures can be used, such as, for example, springs, diaphragms, magnets and the like. In the illustrated embodiment, a helical tension spring 190 biases the valve 178 in the proximal direction against the valve seat 176.

A distal end 192 of the spring 190 passes through the transverse aperture of the valve proximal end 188 to attach the spring 190 to the valve 178. A spider structure 194, similar to that described above in connection with the embodiment illustrated in FIG. 2, supports a proximal end of the spring within the reservoir 164.

FIG. 6 illustrates an alternate control 166 in the form of a screw knob to control the expression of adhesive from the distal delivery end 172 of the applicator 160. As noted above, however, the control 166 can have a variety of forms, including, but not limited to, a button, plunger, piston, and the like.

In the illustrated embodiment, the control 166 includes a plunger 194 disposed within the reservoir. The plunger 194 includes a plurality of annular seals 196. The diameter of each seal 196 is slightly larger than the inner diameter of the housing 168 such that the seal 196 compresses against the inner wall of the tubular housing 168 when the plunger 194 is inserted into the housing 168. The annular seals 196 are disposed upon the length of the plunger 194 so as to provide a generally labyrinth construction to substantially prevent expression of the adhesive from the reservoir 164 in the proximal direction.

The control 166 also includes a cap 198 which defines a hollow interior cavity 200. The interior cavity 200 carries a series of internal threads 202. The internal threads 202 are sized and configured to engage a series of external threads 204 disposed on the proximal end 170 of the tubular housing 168. The pitch of the threads 202, 204 is chosen to control the volume of adhesive expressed at the distal end 172 of the applicator 160, as discussed below.

A rod 206 connects the screw cap 198 to the plunger 194. In the illustrated embodiment, the rod 206 connects the plunger 194 to the screw cap 198 in a manner which permits the screw cap 198 to rotate with respect to the tubular body 168 without rotating the plunger 194. For this purpose, the screw cap 198 includes a center aperture 208 with a portion of the rod 206 piloted into the aperture 208 to permit rotation of the screw cap 198 about the rod 206. The rod 206 also includes a collar 20 which abuts the proximal surface 212 of the interior cavity 200 to prevent the rod 206 from passing through the aperture 208. It is contemplated, however, that the screw cap 198 and plunger 194 can be directly connected so that the plunger 194 rotates with the screw cap 198.

The distance between the proximal surface 212 of the screw cap interior cavity 200 and the proximal end 170 of the tubular housing 168 limits the amount of adhesive which can be expressed through the valve 178. The screw cap 198 preferably also includes an indexing system, which indicates the extent of travel of the screw cap 178, and thus the volume of adhesive expressed. For instance, the screw cap may be rotated such that at specific intervals of rotation the screw cap snaps or clicks into an index position.

For this purpose, as illustrated in FIG. 6b, the cap 198 may carry one or more tangs 214, which extend radially inward from the threaded inner surface of the interior cavity 200. The tubular body 168 may also include at least one longitudinal groove 216, which releasably receives the tang of the cap 198. In the illustrated embodiment, as the cap 198 is rotated, the tang 214 snaps into the corresponding groove 216 on the tubular housing 168 for each quarter turn of rotation (i.e., 90° rotation) of the screw cap 198.

It is understood that the tubular housing 168 may include more or less longitudinal grooves spaced about the circumference of the housing 168 to indicate specific incremental degrees of rotation. For instance, the housing 168 may include three grooves equally distanced from one another so as to define 120° rotation of the screw cap 198. By selecting an appropriate thread pitch and indexing the degree of rotation, the control 166 can indicate the volume of adhesive expressed at the distal end 172 of the applicator 160.

The volume of adhesive expressed will be equal to the axial displacement of the plunger 194 multiplied by the cross-sectional area of the reservoir 164. The axial displacement of the plunger 194, in turn, is directly proportional to the pitch of the threads multiplied by the number of revolutions of the screw cap 198. Thus, for example, where the thread pitch is 0.5 mm, the number of revolutions of the screw cap 198 is 2, and the cross-sectional area of the reservoir 164 is 28 mm², the expressed volume of adhesive will be about 28 mm³.

The distal end 172 of the housing 168 defines a cavity 220 in which the patch 150 is received. The patch 150 has a diameter substantially equal to the inside diameter of the cavity 220, and preferably slightly larger than that of the cavity 220 so as to form a slight interference fit with the wall of the cavity 220. The longitudinal length of the cavity 220 is preferably greater than the thickness of the patch 150 such that a small space exists between the patch 150 and the distal end 172 of the tubular housing 168. It is preferred that the patch 150, before application, is positioned within the cavity 220 against the application surface 162 of the valve 178.

At the time of application, the patch 150 desirably is presaturated with tissue adhesive before applying the patch 150 to the perforation site. For this purpose, the cavity 220 has a sufficient size such that a small volume of adhesive can be expressed through the valve 178 and into the distal cavity 220. In an exemplary embodiment, the cavity 220 has a volume of about 1 mm³ with a patch 150 having a thickness of 0.1 mm. The volume of expressed adhesive is sufficient to substantially saturate the sealant patch 150. In the case of a patch which is not readily saturated with adhesives, flow paths such as small notches on the periphery of the patch will permit adhesive to flow around the distal side of the patch.

A release layer 222 prevents the expressed adhesive from escaping from the distal end 172 of the applicator 168 before application. The release layer 222 desirably adheres to the annular distal end surface of the tubular housing 168 and not to the sealant patch 150. The release layer 222 also includes a tab 224 to facilitate removal of the release layer 222 from the applicator 168. Preferably, the release layer comprises teflon or polyethylene. The release layer 222 is later removed before application of the patch 150 to the puncture site.

To express adhesive into the cavity 220 initially, and onto the applicator surface 186 at the time of application, the controller knob 196 is rotated in a direction which causes the plunger 194 to move distally. Distal movement of the plunger 194 forces the adhesive within the reservoir 164 through the valve seat aperture 182, causing the valve 178 to open. Adhesive expresses through the valve 178 and into the cavity 220. Adhesive fills the cavity 220 and saturates the protective patch 150 contained therein.

As discussed more fully below, the patch 150 is applied over the perforation site. The tissue adhesive will harden virtually on contact to secure the patch 150 over the perforation and to seal the patch.

Figure 7:
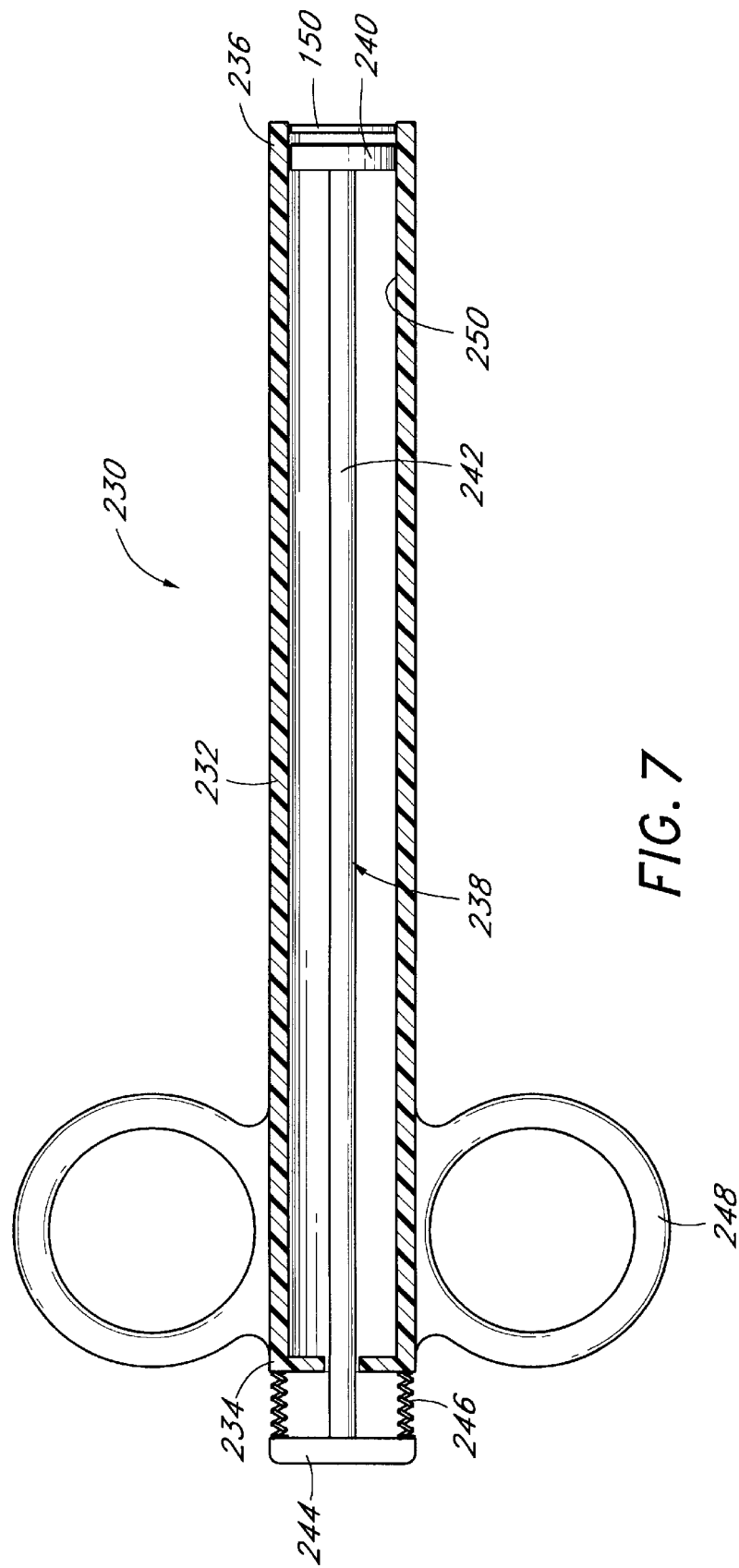
FIG. 7 is a sectional side view of an applicator in accordance with a further embodiment of the present invention.

FIG. 7 illustrates an additional embodiment of an applicator 230 for use with a sealant patch 150 pretreated with a tissue adhesive.

The applicator 230 includes a tubular body 232, having a proximal end 234 and a distal end 236, and an actuator mechanism 238 formed by a distal plunger 240, a linkage rod 242, and a proximal push button 244. Springs or other biasing mechanisms 246 bias the push button 244 to a position spaced from the proximal end 234 of the housing 232.

The applicator 230 also can include gripping structure to ease handling and manipulating the applicator 230. For this purpose, in the illustrated embodiment, the applicator 230 includes a pair of rings 248 located near the proximal end 234 of the applicator 230. It is understood that other types of conventional gripping structures could be used as well.

A sealant patch 150, of the type described above, is disposed at the distal end 236 of the applicator 230. The sealant patch 150 has a diameter substantially equal to the diameter of the tubular housing 232, and more preferably slightly larger so as to form a slight interference fit within the interior wall 250 of the applicator housing 232. Alternatively, radially inwardly directed ridges or other surface structures can removably retain the patch 150 as will be appreciated by one of skill in the art.

The sealant patch 150, as noted above, may be precoated with an adhesive which hardens virtually on contact with tissue to permanently bind the sealant patch 150 to the tissue over the puncture site. Any of the variety of tissue adhesive discussed above can be used. It also is contemplated that an adhesive coating may be applied to the ablumenal side of the patch 150 just before application. Preferably, with most cyanoacrylate adhesives, adhesive will be applied to the patch just prior to the implantation of the patch.

The application of the adhesive coating can occur by direct application of the adhesive to the patch 150, by dipping the distal end of the applicator 230 into a reservoir of adhesive, or by contacting the patch 150 with fluid permeable membrane or absorptive blotter material saturated with adhesive.

In operation, the delivery end 236 of the applicator 230 is placed near or in contact with the tissue surface surrounding an opening therein, and the control 244 is activated to dislodge the adhesive patch 150 from the distal end 236 of the applicator 230. The patch 150 is placed in contact with the tissue surface over the perforation site.

As noted above, this method can be used to close any exposed surface which can be reached by any of the above-described applicators. For instance, the above-described applicators may be used in open laparotomy for closing the peritoneal surfaces of various hollow viscera, diaphragm and omentum. The sealant patch 150 applied by the applicator also has the potential of sealing the surface of the liver or spleen, or used to seal perforated lungs, hearts, or pleura. It may also be used to seal a perforation of a vascular lumen, such as an artery or vessel.

In this latter application, the present invention also includes a preferred method for inhibiting arterial bleeding at the arterial access site after percutaneous transluminal procedures, such as, for example, angioplasty, angiography, coronary angiography, atherectomy, or similar procedures.

FIGS. 8 through 12 schematically illustrate a series of method steps involved with a preferred method of inhibiting arterial bleeding at the arterial access site. For illustrative purposes, this method will be described as involving the use of an applicator comprising an elongate body with an angled patch surface on its distal end to conform to the surface of the artery. However, it is understood that other types of applicators, including the other embodiments described above, for delivering adhesive alone or a patch, can be used as well.

In a representative PTCA procedure, the position and axial orientation of a vascular structure, for example, the femoral artery, is determined tactily using three adjacent finger tips. An introduction needle is inserted at about 30° into the artery using finger pressure against the artery upstream of the puncture to stop blood flow.

A short introduction guidewire is passed through the introduction needle and into the artery and the needle is withdrawn leaving the guidewire in position. Next, first and second sheaths, usually an introducer sheath and a dilator sheath, are passed over the guidewire and inserted into the vascular structure as is well known. The dilator sheath is removed leaving the introducer sheath in place to provide arterial access. A guidewire is threaded through the sheath and transluminally to the desired treatment location. Then the balloon catheter or other instrumentation is inserted through the introducer sheath and threaded over the guidewire to a desired location, such as an atherosclerotic plaque.

Once the intravascular procedure has been completed, the catheter is removed. The usual method of hemostasis involves also removing the introducer sheath and guidewire, and applying pressure to the perforation site through the skin until hemostasis has occurred. Alternatively, an obturator may be inserted into the introducer sheath and both obturator and introducer sheath left in place for a period of time, prior to their removal. This additional step depends on the type of procedure and the patient's state of coagulation among other variables.

Referring to FIGS. 8 through 12, arterial catheterization commonly involves perforating a wall 260 of the vessel 262 such as, for example, the femoral artery, by introducing a needle percutaneously into the vascular structure. Various sheaths, catheters or other instrumentation are introduced through that puncture, as desired, to accomplish the medical procedure. Following the procedure, the guidewire and/or a tubular introduction sheath can be left in the artery to permit the puncture closure method of the present invention.

Figure 8:
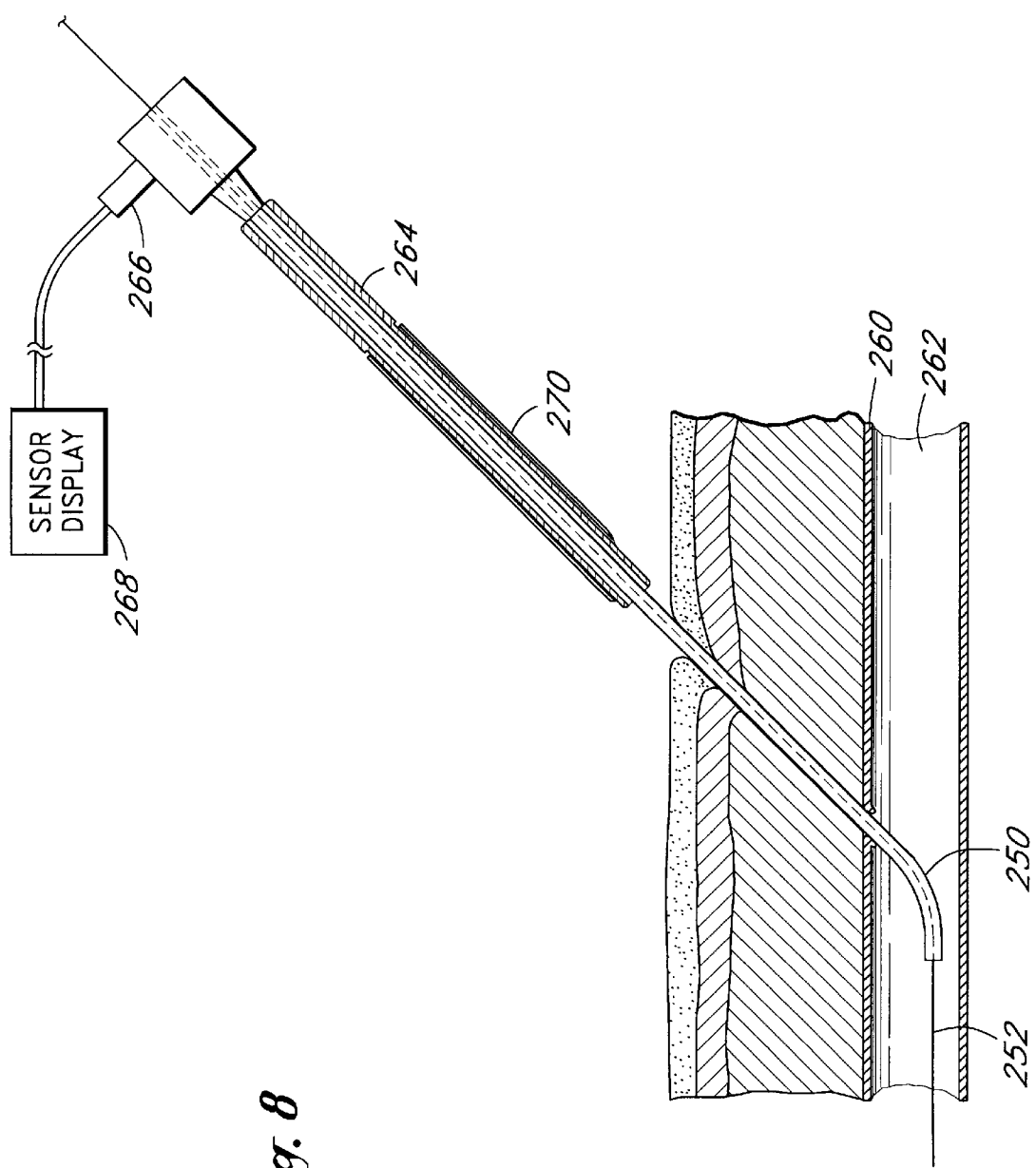
FIG. 8 is a schematic representation of a catheter introduction sheath having a tissue expander cannula and introducer cannula thereon, in position within an artery.

With reference to FIG. 8, an introducer sheath 250 having a guidewire 252 extending there through is in position within the vascular structure 262. The introducer 250 may have been left in place following the vascular catheterization procedure, or may have been introduced subsequently for the purpose of the present vascular patching procedure.

During catheterization procedures, blood pressure is commonly measured at the arterial access site. As seen in FIG. 8, a pressure sensor display 268 is connected to a side port 266 on the introducer 250.

As illustrated in FIG. 8, the tubular sheath 250 is in one embodiment of the present invention modified by carrying an expander cannula 264 having a introducer cannula 270 slidably mounted thereon. The expander cannula 264 and introducer cannula 270 in this embodiment are mounted on the sheath 250 prior to commencement of the catherization procedure. In this embodiment, the catherization (e.g. balloon dilatation, drug delivery etc.) is conducted through the sheath 250 having the expander cannula 264 and introducer cannula 270 thereon throughout.

In an alternate embodiment of the invention, the expander cannula 264 is provided in two halves, and adapted to be mounted upon the sheath 250 at the clinical site. If the physician prefers the maneuverability of the sheath 250 without the expander cannula 264 and introducer cannula 270 thereon, he can use a standard cannula 250 for the catherization procedure. At the completion of that procedure, a two or more part expander cannula 264 is reassembled around the introducer sheath 250, and advanced distally along the sheath 250 in accordance with the procedure discussed below. Once the expander cannula 264 is in position against the outer wall of the artery as discussed below, the sheath 250 may be removed, and the distal end of the introducer cannula 270 is advanced over the proximal end of the expander cannula 264 and distally until it is appropriately positioned against the wall of the artery. At that time, the expander cannula 264 can be removed proximally leaving the introducer cannula 270 in place, and ready for the adhesive or adhesive patch application as discussed below.

The split expander cannula of the present invention can be manufactured in a variety of ways, as will be apparent to one of skill in the art. For example, the expander cannula described above and illustrated in FIGS. 15 and 16 can be cut in two halves along an axially extending plane. Preferably, releasable interlocking structure are provided for retaining the two halves in an assembled configuration. For example, pins can be provided on one half of the expander cannula for engaging corresponding recesses on the other half of the cannula. Any of a variety of "snap fit" interlocking structures can be utilized, to accomplish the advantages of the present invention.

Preferably, unlike the embodiment illustrated in FIGS. 15 and 16, the split expander cannula is provided with a substantially uniform outside diameter throughout its entire length. This facilitates mounting the distal end of the introducer cannula over the proximal end of the expander cannula, so that the introducer cannula can be advanced distally along the expander cannula into the appropriate position such as that illustrated in FIG. 10.

Although the split expander cannula described above is described in terms of two opposing halves, the expander may be constructed from any of a variety of pieces which are reassembleable over the sheath into a generally tubular structure. Thus, three or more axially extending segments can be provided for reassembly into a unitary tubular structure. In the preferred embodiment, two halves are provided, which may be snapped fit together at both contact points. Alternatively, the two halves may be joined by an axially extending hinge such as a section of flexible material, so that the hinged expander halves can be positioned around the sheath 250 and then closed thereon to form a tubular expander.

With reference to the embodiment illustrated in FIG. 8, the introducer 250 is withdrawn from the vascular structure 262 to a location where its distal end is adjacent to the ablumenal surface of the vessel wall 260. See FIG. 9. The blood pressure display 268 aids in the proper positioning of the introducer 250 at this location. A surgeon, or like operator, slowly withdraws the introducer 250 from the vessel while monitoring the blood pressure displayed by the blood pressure display 268. The blood pressure significantly drops once the distal end of the introducer 250 is completely withdrawn from the vessel and the perforation shrinks to its nondilated size. In this manner, the operator knows when he or she has withdrawn the distal end of the introducer 250 to a position adjacent to the ablumenal surface of the vessel 262 as illustrated in FIG. 9.

Figure 9:
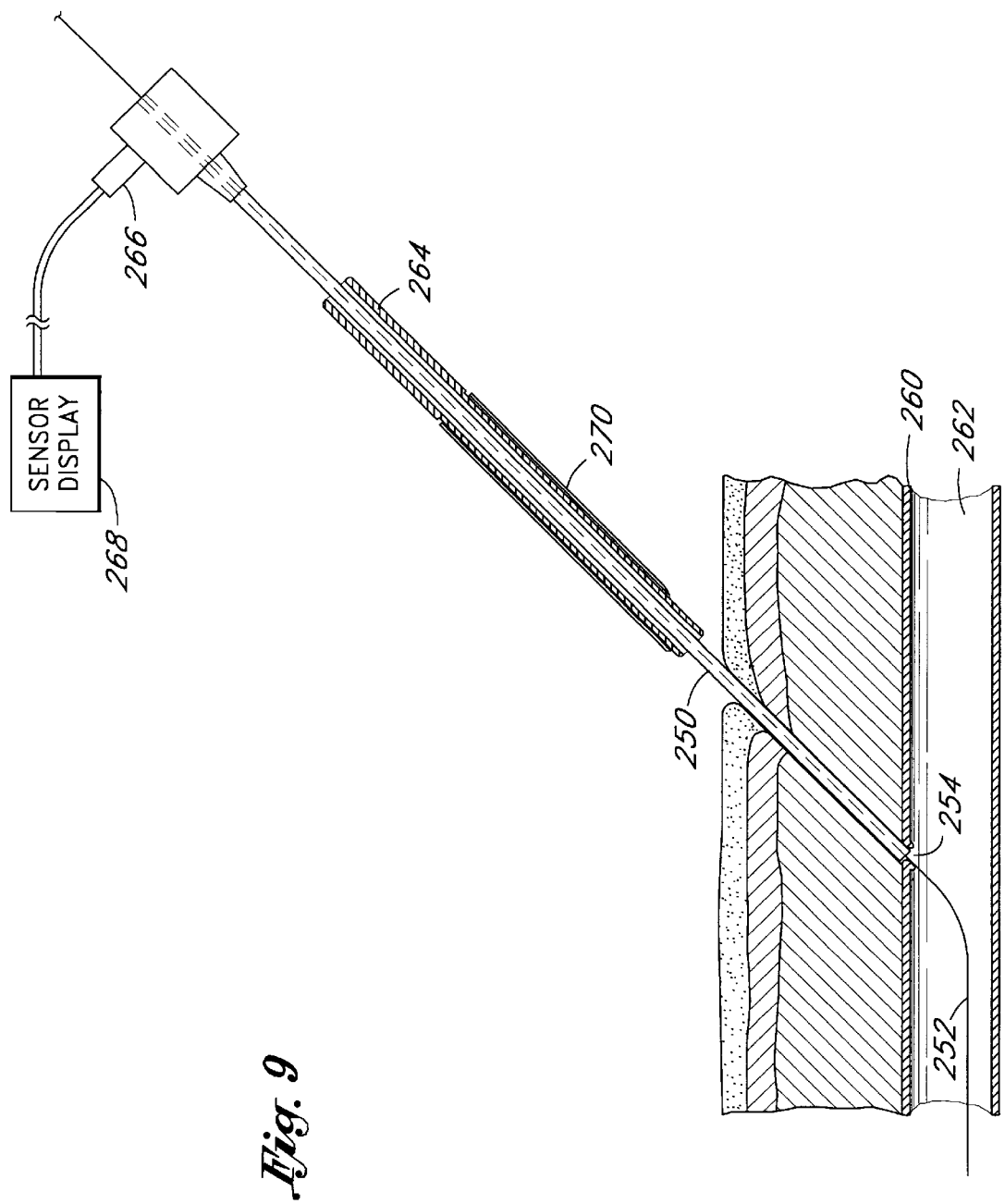
FIG. 9 is a schematic illustration as in FIG. 8, with the catheter introduction sheath withdrawn from the artery.
Figure 10:
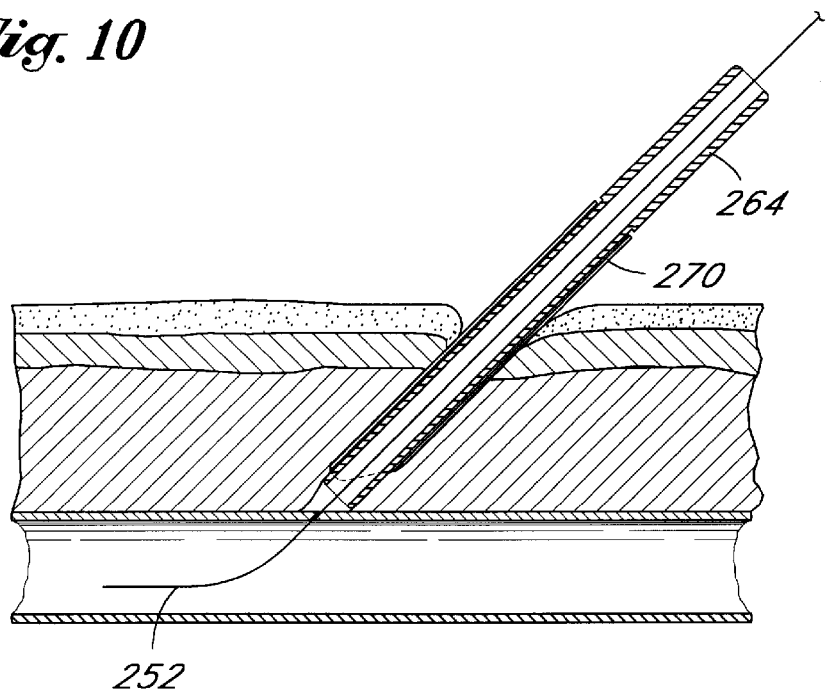
FIG. 10 is a schematic representation as in FIG. 9, with the introducer cannula and expander cannula in position against the artery wall.
Figure 11:
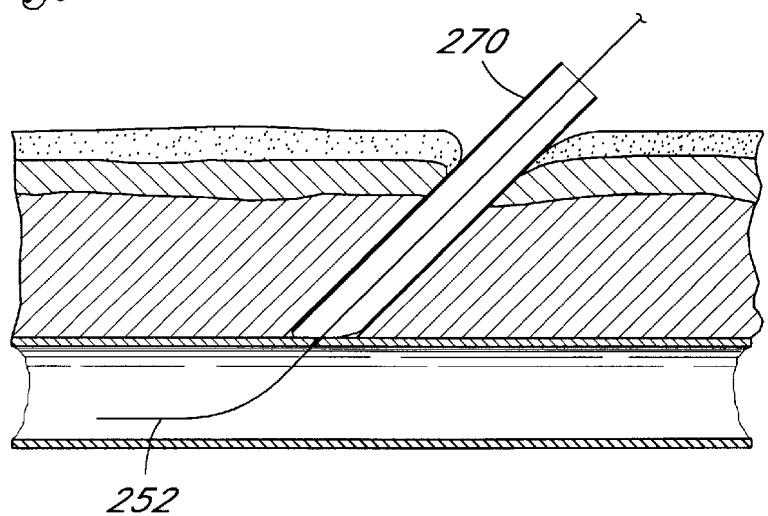
FIG. 11 is a schematic representation as in FIG. 10, with the expander cannula removed.

With reference to FIGS. 9–11, the assembly of the expander cannula 264 and introducer cannula 270 is advanced distally along the catherization sheath 250, until the distal end 265 of the expander cannula 264 contacts the vessel wall. Contact with the vessel wall can be determine by tactile feedback to the operator. Alternatively, indium such as a line or other marking drawn around the outer circumference of the sheath 250 can be positioned such that it becomes visible to the operator when the expander cannula 264 has been advanced sufficiently distally that the distal end 265 of expander cannula 264 is at the surface of the vessel.

Once the distal end 265 of expander cannula 264 is in position against the exterior wall of the vessel 262, the sheath 264 can be removed to produce the assembly schematically illustrated in FIG. 10. Preferably, the guidewire 265 remains in place.

In the illustrated embodiment, once the introducer cannula 270 is seated against the vessel wall, the expander cannula 264 may be proximally withdrawn, to produce the assembly illustrated schematically in FIG. 11. In an alternate embodiment, the function of the expander cannula 264 and introducer cannula 270 can be combined into a single device. A variety of specific structural modifications can be made, in view of the disclosure herein, by one of ordinary skill in the art in view of the objective to properly positioning the introducer cannula 270 against the vessel wall.

One embodiment of an introducer cannula 270 and dilator cannula 264 is shown in FIGS. 13–16. The cannula 270 has a proximal end 272, a distal end 274, and a minimum inner diameter, which is greater than the maximum diameter of the perforation 276 in the vessel wall 260. The cannula 270 also desirably has a minimum inner diameter, which is greater than the maximum external diameter of the patch applicator 80 or adhesive applicator. This feature allows the patch and/or adhesive applicator to axially, movably fit within the cannula 270.

Preferably, the distal end 274 of cannula 270 is provided with an atraumatic tip 278 to minimize damage to the vessel or surrounding tissue. Distal end 274 is preferably also provided with an angled cut 280 which facilitates placement against the vessel wall at an introduction angle of about 30°.

Preferably, the distal end 274 of the cannula 270 has a sufficient diameter to expose both the perforation 254 and a sufficient area of adjacent vessel wall surrounding the perforation 254 so that a sufficient overlap by the patch can be achieved. For a typical PTCA arterial perforation 254, having a diameter of about 1 mm, an introduction cannula 270 having an inside diameter of about 3 mm and an outside diameter of about 4 mm at its distal end 265 may conveniently be used.

Alternatively, the function of introducer cannula 270 can be readily accomplished by a structure integrally formed or secured to the applicator 80. For example, the delivery surface 86 can be retractably disposed within an outer tubular housing, as will be readily appreciated by one of skill in the art in view of the disclosure herein.

Figure 12:
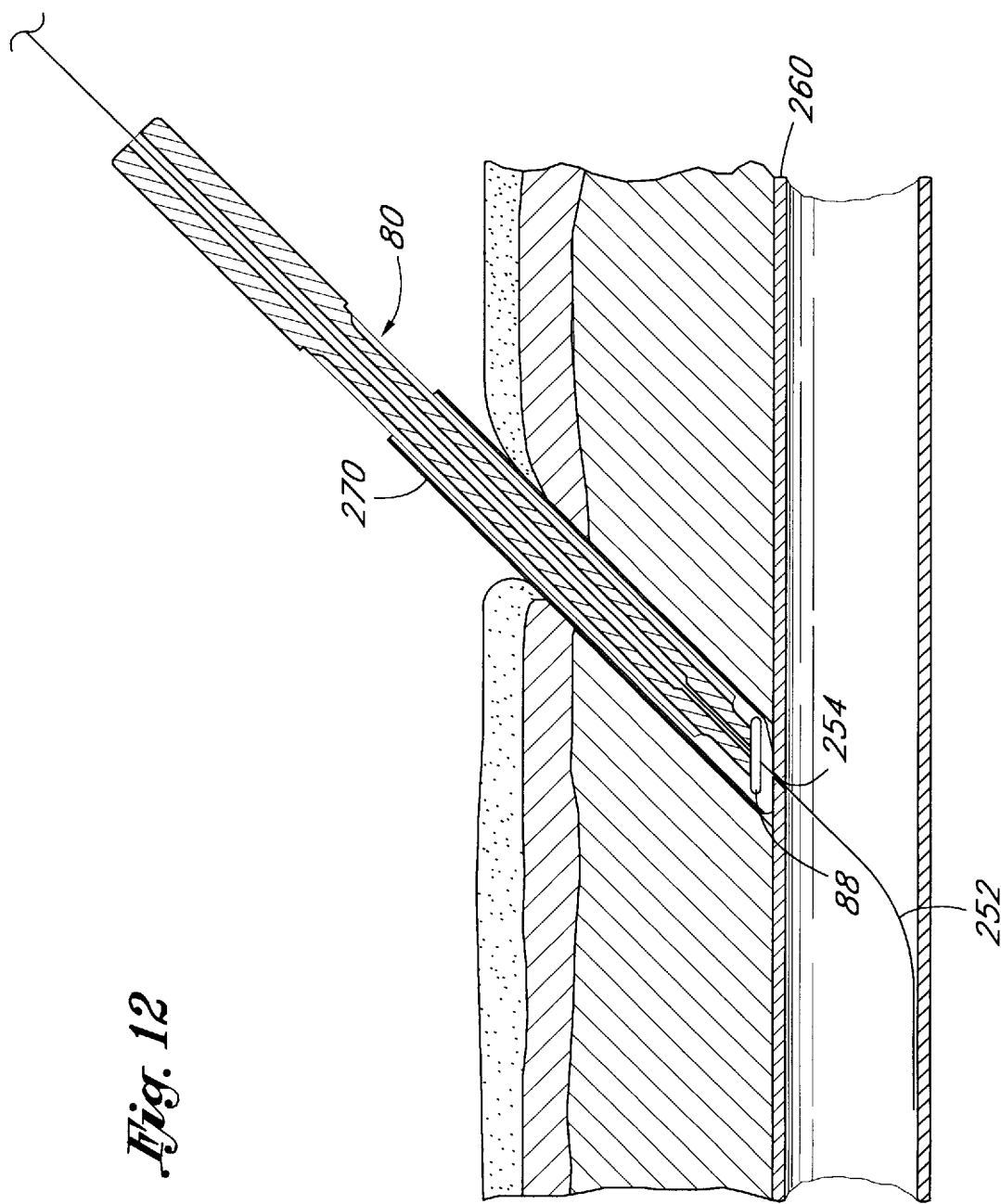
FIG. 12 is a schematic representation as in FIG. 11, with a vascular patch applicator advancing distally through the introducer cannula towards a vascular perforation.

At the point in the procedure illustrated at FIG. 11, the site is prepared for the application of an adhesive patch 88 (FIG. 12). Patch 88 is preferably secured to a patch applicator 80 (FIG. 12), as has been previously discussed. Attachment of the patch 88 to the applicator 80 can be accomplished such as through the use of a relatively weak adhesive bond or mechanical interfitting. In one embodiment, the patch 88 is preassembled onto the applicator 80, such as at the point of manufacture, by placing a relatively short shipping guidewire through the patch and into the guidewire lumen of applicator 80. This shipping guidewire may be provided with a distal anchor, such as a T or other configuration, to prevent the patch 88 from advancing off the end of the shipping guidewire. The proximal end of the shipping guidewire extends into the guidewire lumen and possibly out the proximal end of the applicator 80. When ready for use, the shipping guidewire can be removed by gripping the anchor portion or other structure and pulling it from the guidewire lumen. The proximal end of the procedure guidewire 252 is then threaded into the patch 88 and distal end of applicator 80 as illustrated in FIG. 12.

Once a patch 88 is positioned on a patch surface 86 of a patch applicator 80, adhesive can be applied to the patch in any of a variety of ways. In accordance with one aspect of the present invention, the adhesive is applied using an adhesive delivery kit of the type illustrated in FIG. 6. Alternatively, adhesive can be manually applied to the tissue contacting surface of the patch 88 such as by the use of a squeeze tube, dropper, or other structure by the medical personnel at the time of the procedure. As a further alternative, any of the adhesive applicators disclosed herein can be used in the methods of the present invention to apply an adhesive seal, without implanting a vascular patch.

In a typical procedure, the proximal end of a guidewire 252 extends through the perforation and out of the cannula 270. This may be a guidewire inserted for the purpose of the vascular patch procedure, or, more likely is the guidewire which was utilized in the original catherization. The patch applicator 80 having the patch 88 thereon is advanced over the proximal end of the guidewire, and advanced down the guidewire towards the patient. If the adhesive is manually applied to the patch, that application may be accomplished following threading the patch 88 and applicator 80 onto the guidewire.

The operator then advances the applicator 80 along the guidewire and through the cannula 270 until the patch 88 contacts the vascular wall 260 without penetrating the perforation 254. See FIG. 12. The operator tactily feels and recognizes when the patch 88 contacts the ablumenal surface of the vessel wall 260.

As an alternative to tactile feedback once the introducer 270 has been properly positioned, the applicator 80 can be provided with visual or mechanical indicia which indicate that the appropriate depth has been reached. For example, applicator 80 can be provided with a mark or line around its circumference indicating the axial depth to which it should be advanced in a distal direction, before the mark disappears within introducer 270. Similarly, the applicator 80 can be advanced distally into the cannula 270 until a physical stop on the applicator 80 reaches the proximal end of the introducer 270.

The operator thereafter withdraws the applicator 80 from the cannula 270 after applying the patch 88 and tissue adhesive. The tissue compresses around the deposited patch 88 and percutaneous perforation. The tissue may be taped or bandaged subsequently with or without the application of a tissue adhesive to facilitate the physiological healing of the muscular and cutaneous tissue at the access site.

A modified kit and methods of its use are disclosed in FIGS. 17 through 22. Referring to FIG. 17, there is disclosed a schematic view of an introducer sheath 300 in position within an artery (or other vessel or hollow organ) 302. Any of a variety of known introducer sheaths may be used, such as that marketed by the U.S.C.I. Division of C.R. Bard. Introducer sheaths are typically provided with a side port 309, which may be valved, which can be used for irrigation or blood pressure monitoring as will be discussed. Suitable sheaths for accessing the femoral artery generally have a length of about 10 cm, an outside diameter of about 3 mm and an inside diameter of about 2.5 mm. Other dimensions can also be used, as long as the sheath accomplishes its purpose of providing access for the purposes disclosed herein while preferably minimizing trauma at the entry site.

Prior to leaving the catheter lab following a typical percutaneous transluminal coronary angioplasty or other transluminal procedure, the patient is left with the sheath 300 in position as shown in FIG. 17. In accordance with the present invention, rather than removing the sheath 300 and accomplishing conventional closure procedures, a guidewire 304 is advanced transluminally through the sheath 300 and into the artery 302. Blood flow may be stopped or inhibited by manual pressure against the skin 301 such as by finger 303 to compress the artery 302 on the upstream side of the puncture.

Figure 18:
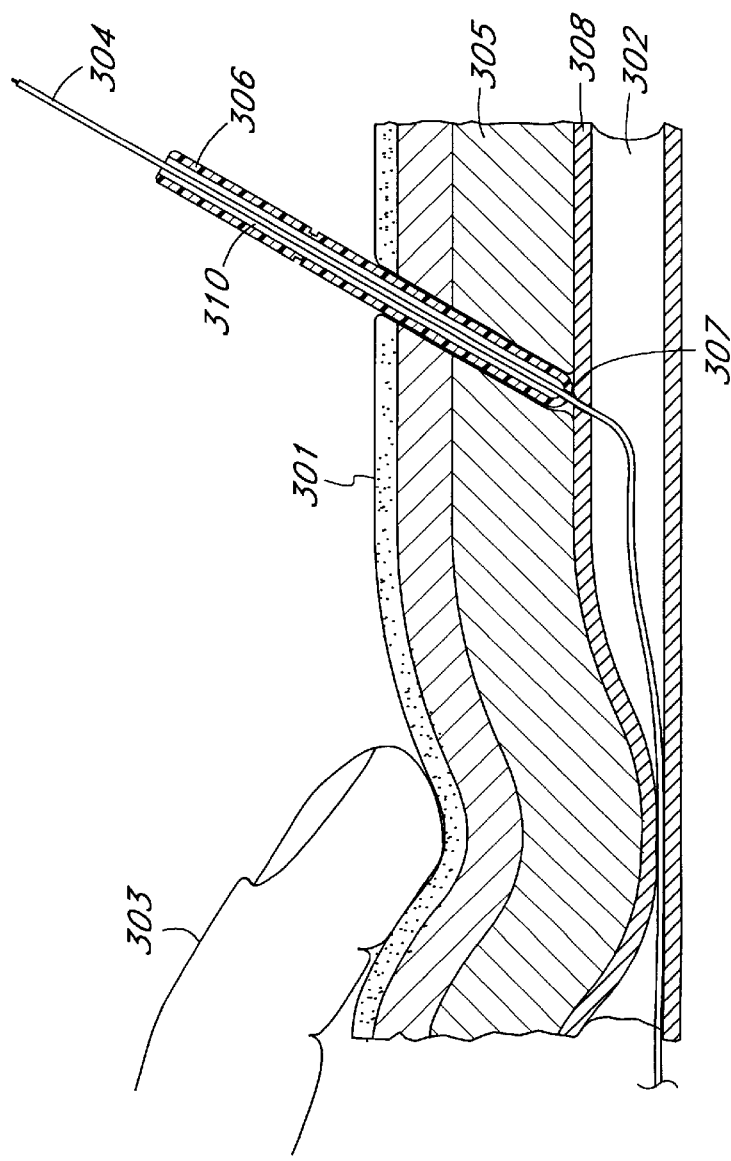
FIG. 18 is a schematic representation of an introducer sheath in position against the vessel wall.

The sheath 300 is thereafter removed proximally from the patient while leaving the guidewire 304 in place. Referring to FIG. 18, a tissue expander 306 is threaded over the guidewire 304 and advanced distally through the tissue 305 until the distal end 307 of the tissue expander 306 contacts or encounters resistance from the arterial wall 308. At that point, the clinician can feel resistance to further distal advance of the tissue expander 306, and knows that the tissue expander 306 has been placed adjacent the arterial wall 308.

Tissue expander 306 generally comprises an elongate tubular body, having a central lumen 310 extending axially therethrough. The distal end 307 of the body is provided with a generally blunt atraumatic tip. That tip may be rounded such as in a hemispherical configuration. Tip 307 may also be angled with respect to the longitudinal axis of the expander 306, to compliment the conventional angle at which the puncture resides with respect to the wall 308 of the vessel 302.

In one particular embodiment, the tissue expander 306 had an axial length of about 8 cm, and a circular cross section having an outside diameter of about 0.200 inches. The central lumen had an inside diameter of about 0.040 inches. The tissue expander 306 can be produced from rod stock, tube stock or can be formed by injection molding or other techniques known in the art. Any of a variety of materials may be used, including metals such as stainless steel, or plastics such as medical grade polyethylenes and others known in the art. The precise dimensions and construction materials of the tissue expander can be varied widely and still accomplish the objectives of the present invention, provided that the tissue expander 306 is dimensioned to cooperate with the other components of the sealing kit, and is adapted for use in the closing of a percutaneous vascular puncture.

Following placement of the tissue expander 306, a tissue speculum 312 (see FIG. 19) is positioned coaxially about the tissue expander 306 and advanced distally until a distal end 314 of the speculum contacts the vessel wall 308.

Figure 19:
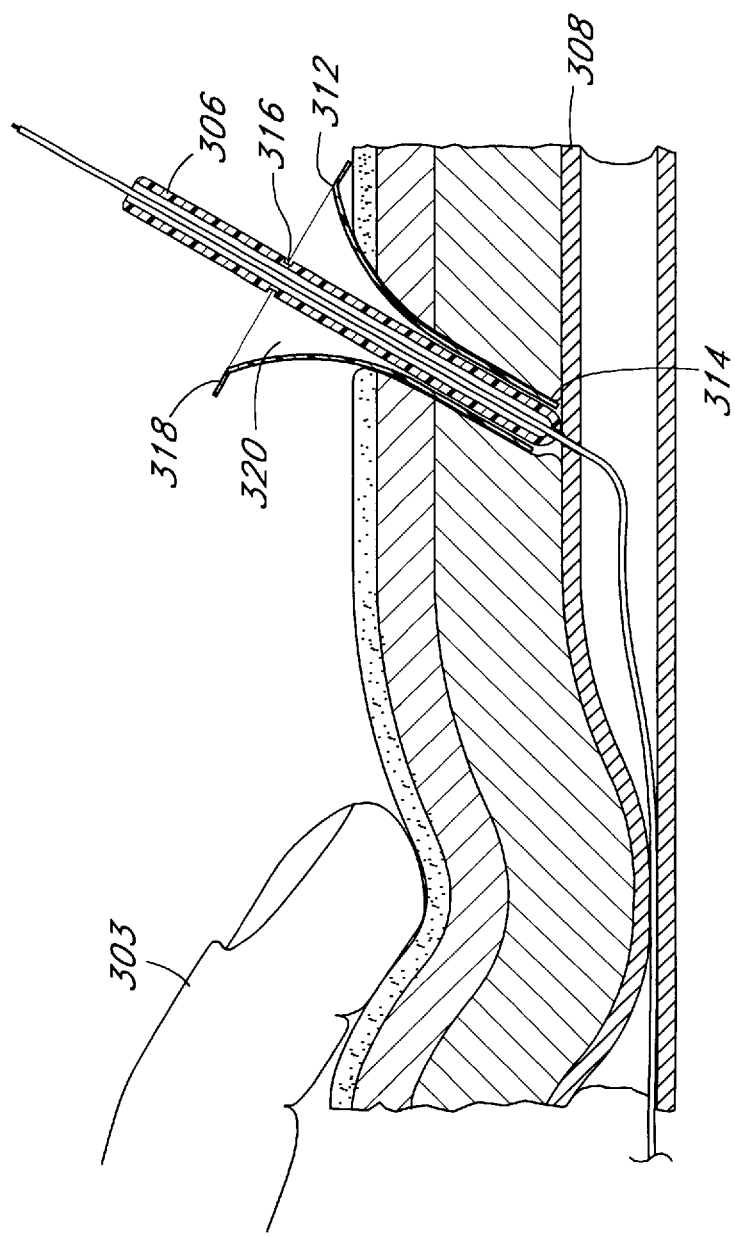
FIG. 19 is a schematic representation as in FIG. 18, with a tissue speculum in position against the vessel wall.

In the embodiment illustrated in FIG. 19, the speculum 312 is generally in the shape of a conventional funnel, having a relatively large diameter proximal end 318 and a relatively small diameter distal end 314. A central lumen 320 extends axially throughout the speculum 312. The minimum inside diameter of the lumen 320 is sufficient to permit the speculum 312 to be advanced coaxially over the tissue expander 306 as illustrated in FIG. 19. In one embodiment, the speculum 312 comprises polyethylene, having a proximal outside diameter of about 1 inch and an axial length of about 5 cm. The distal inside diameter was about 0.220 inches, to accommodate a tissue expander 306 having an outside diameter of about 0.200 inches.

The speculum 312 can be manufactured in any of a variety of ways known in the art, such as injection molding. Suitable construction materials include various medical grade polyethylenes.

Alternatively, the function of the tissue expander 306 and speculum 312 can be accomplished by a single adjustable tissue retractor which both tracks the introducer sheath and provides access to the puncture in the vessel wall. For example, both functions can be accomplished by the retractor 344 illustrated in FIG. 23. In general, the retractor 344 comprises a proximal control end 346 and a distal speculum end 348. Proximal end 346 preferably comprises a hemostat like pair of finger rings 350 and 352 as is known in the art. The speculum end 348 preferably comprises two speculum halves 354 and 356 connected to the finger rings 350 and 352 by frame components 358 and 360. Frame components 358 and 360 are pivotably secured together by a hinge 362.

Pressing finger rings 350 and 352 towards each other causes speculum halves 354 and 356 to move apart from each other such as to permit visualization therethrough of the vessel wall. A ratchet 364 is provided to maintain the speculum halves 354 and 356 spread apart at the distance selected by the clinician.

An alternate retractor is shown in FIG. 24. A thumb screw 366 is rotatably linked to a threaded shaft 368. The shaft 368 is freely rotatable within a first frame 370 but threadably engages a second frame 372. A spring, such as a coil spring 374 is optionally also provided to bias the tissue expander in the closed direction. The clinician can rotate the thumb screw 366 to open the retractor to any desired diameter.

The use of one of the retractors permits greater flexibility in the method of the present invention. For example, the clinician can adjust the exposed area of the vessel by simply advancing the retractor percutaneously towards the vessel and manipulating the control rings 350 and 352 or thumb screw 366. In some procedures, it may be desirable to expose a sufficient area on the vessel to allow direct visualization of the implanted patch. This would allow the clinician to visually evaluate whether the patch has been positioned properly over the puncture in the vessel wall. In addition, the use the retractor 344 may permit sufficient expansion of the percutaneous puncture that the vessel can be clamped upstream of the puncture such as through the use of conventional hemostats.

The proper positioning of the speculum 312 or retractor can be determined through tactile feedback, for example, at the point that the distal end 314 of the speculum 312 contacts the vessel wall 308. Alternatively, the tissue expander 306 when used may be provided with an indicium 316 such as an annular groove or stripe. See FIG. 19. When the indicium 316 is axially aligned with a reference point on the speculum 312, such as the proximal end 318, the clinician will know that the speculum 312 is in a proper position relative to the tissue expander 306.

Following placement of the tissue speculum 312, the tissue expander 306 may be removed proximally from the guidewire 304 and discarded in the case of a one-time use disposable embodiment. In general, any or all of the components herein except the patch may be produced in either a one-time use disposable form or in a form adapted to be sterilized and reused, as desired.

Referring to FIG. 20, the patch applicator assembly 322 is provided. The patch applicator 322 generally comprises a patch applicator 324 having an axially extending lumen 326 extending therethrough. A distal surface 328 on the patch applicator 324 is generally angled with respect to the longitudinal axis of the patch applicator 324 to rest generally parallel to the arterial wall 308 when the patch applicator 324 is advanced through a conventionally angled puncture as has been discussed. In addition, the surface 328 may be provided with a curvature such that the surface 328 might generally conform to a portion of the wall of a cylinder. The curvature of the surface 328 has a longitudinal axis which is parallel to the vessel in the installed orientation. In this manner, surface 328 complements the curved vessel wall 308.

A second, optional component to the patch applicator assembly 322 is a cannula 330. Cannula 330 is an elongated tubular body having a proximal end 332, a distal end 334 and a central lumen 336 extending therethrough. Preferably, the proximal end 332 is provided with a handle 338 thereon. In the illustrated embodiment, the cannula 330 comprises a section of hypodermic needle tubing, having an inside diameter of about 0.020 inches, an outside diameter of about 0.035 inches, and a length of about 6 inches.

In a preferred embodiment, the guidewire 304 is configured to couple to the distal end 334 of the cannula 330 but the cannula 330 cannot advance distally over the wire to the vascular puncture site. In this embodiment, the guidewire has a length of about one or two feet, and comprises an elongated flexible body having about a 0.035 inch outside diameter. The Radiofocus Guidewire M, available from Terumo Corp., Tokyo, Japan has been found to be suitable for present purposes. Other dimensions can also be used, as will be apparent to those of skill in the art.

The proximal end of the guidewire is provided with a step down in diameter in the proximal direction from the approximately 0.035 inch outside diameter to a short proximal projection 305 of the core wire which may be a nitinol or other metal wire having a diameter of about 0.015 inches. That core wire is a sufficiently small diameter to be fit within the central lumen 336 extending through cannula 330. Thus, the distal end 334 of the cannula 330 may be coupled to the proximal end of the guidewire 304 by advancing the proximal projection 305 on the guidewire 304 into the central lumen 336 at the distal end 334 of the canula 330 as illustrated in FIGS. 20a and 20b. The patch applicator 324 carrying one or more patches thereon can then be advanced distally over the cannula 330 and along guidewire 304 to the patch application site.

In use, one or more vascular patches 340 are provided. Vascular patch 340 may comprise any of a variety of materials suitable for adhesion to a vessel wall, for placement within the human body. In a preferred embodiment, the patch comprises a bioabsorbable material such as Gelfoam™, marketed by the Upjohn Company. Gelfoam is available in sheets, and may be stamped to produce patches of the appropriate dimensions. Gelfoam patches will be completely absorbed within about one to two weeks following implantation.

In a preferred embodiment, the patch 340 is cut from a sheet of Gelfoam having a thickness of about 2 mm. The patch is preferably oval or elliptical in shape, having a long axis length of about 0.300 inches, and a width of about 0.200 inches. Alternate patch materials and dimensions can be readily used by those of skill in the art in view of the disclosure herein.

At least one and preferably two patches 340 are provided with a central aperture and positioned over the cannula 330 as illustrated in FIG. 20. To minimize the risk of patch adhesion to the patch applicator 324, a small amount of a material such as petroleum jelly can be placed between the proximal patch and the distal surface 328 of patch applicator 324. In addition, the use of two patches further minimizes the risk of adhesion between the distal most patch and the patch applicator 324.

The patch application assembly 322 may then be connected to the proximal end of the guidewire 304. Once connected, the patches 340 can be advanced distally along the guidewire and down to the vessel wall using the applicator 324 as illustrated in FIG. 21.

Prior to advancing the patches from the proximal position illustrated in FIG. 20 to the distal, implanted position illustrated in FIG. 21, a quantity of a tissue adhesive such as a cyanoacrylate is preferably applied to the distal surface of at least the distal most patch 340. As has been discussed, certain of the cyanoacrylates, such as the ethyl-2-, the n-butyl-2 or the iso cyanoacrylates may be preferred at the present time. Preferably, the cyanoacrylate is mixed with Cabosil to act as a thickening agent to improve the retention of the adhesive on the patch and permit the formation of a "skin" to facilitate transport of unsolidified adhesive through an aqueous environment. Other thickeners, stabilizers, or other additives may be added, such as polymethyl methacrylate, hydroquinone and others deemed desirable by one of skill in the tissue adhesives art.

The preferred cyanoacrylate or other instant bonding adhesive will preferably be utilized in the form of a gel such as that obtained by the mixture with Cabosil. The present inventor has determined that the outside of the gel bead forms a skin upon contact with biological fluids which protects the gel surrounded by the skin from polymerizing. As the applicator 324 is pressed gently against the artery, the gel bead ruptures thereby releasing fresh cyanoacrylate gel for boding at the vessel wall. The use of the gel thus forms a delivery vehicle for carrying a quantity of adhesive safely to the application site through a moist environment.

Following application of the tissue adhesive, the patch applicator 324 is advanced distally as illustrated in FIG. 21 to press the patch against the application site. While pressing the applicator 324 against the artery wall 308, the speculum 312 may be removed, followed or preceded by removal of the guidewire 304. The applicator 324 may thereafter be removed, while still maintaining digital pressure on the artery 302. Following a set time, which may be in the area of from about 30 seconds to several minutes and preferably about 60 seconds, manual pressure against the artery 302 is released and bleeding through the puncture should be blocked by the patch 340. The surface wound may be additionally sealed with a drop of cyanoacrylate, and/or dressed in accordance with conventional wound closure techniques.

In accordance with an alternate embodiment of the method of the present invention, a patient having a vascular puncture is selected. The vascular puncture may have been made to provide vascular access to perform any of a wide variety of therapeutic or diagnostic procedures, such as PTCA. Preferably, the tubular introducer sheath utilized to provide vascular access for the medical procedure is left in place to provide vascular access for the purpose of the present puncture closing method. However, the present method can be performed following removal of the introducer sheath, such as by reintroducing a tubular introducer sheath to provide vascular access.

Preferably, a guidewire is either left in place or is introduced through the introducer sheath, through the vascular puncture, and into the vessel. Any of a wide variety of guidewires can be used for this purpose. In one application of the method, for closing a puncture in the femoral artery following a conventional PTCA dilatation, a 0.014-inch diameter guidewire may be used.

A blood pressure sensing device is connected to the tubular introducer sheath to monitor blood pressure at the distal end of the tubular sheath. Conventional introducer sheaths, such as that illustrated in FIG. 17, are provided with a side port 309 which can be used to connect the blood pressure sensing device.

With the blood pressure sensing device in operation, the sheath is slowly withdrawn from the artery until an abrupt drop in blood pressure at the distal tip of the sheath is noted. The abrupt drop in blood pressure signifies that the distal tip of the sheath has exited the artery. At that point the cross section of the arterial puncture will typically rebound to a smaller opening, surrounding the guidewire.

A vascular patch applicator is provided. Generally, the vascular patch applicator is an elongate tubular structure adapted for sliding coaxially over the guidewire towards the vessel. Thus, the patch applicator is provided with an axially extending guidewire lumen having a sufficient inside diameter to slidably receive the guidewire therethrough. The outside diameter of the patch applicator is as large as possible, while permitting the applicator to slide coaxially within the introducer sheath. The patch applicator may, for example, take the form of the patch applicator 324, configured to have an appropriate length and diameter to fit within the introducer sheath. In an application of the invention which uses an introducer sheath with an axial length of about 10 inches and an inside diameter of about 2.5 mm, the patch applicator has a length of at least about 12 inches and an outside diameter of about 2.2 mm.

A vascular patch having a central aperture as has been discussed is threaded onto a proximal end of the guidewire, followed by the distal end of the patch applicator. Alternatively, the patch can be secured to the distal end of the patch applicator and threaded onto the proximal end of the guidewire as a single unit. A tissue adhesive is applied to the distal side of the patch. Preferably, the adhesive comprises a cyanoacrylate gel, as has been discussed. Preferably, the sheath is flushed with saline through the side port 309 to minimize the concentration of red blood cells at or about the vascular puncture site. The patch applicator is used to advance the patch distally over the guidewire and through the introducer sheath towards the artery. While a distal force is applied to the patch applicator to gently press the patch against the artery wall, the guidewire and the introducer sheath may be removed. After a brief interval, such as 10 or 20 seconds or more, the patch applicator may be removed, leaving the patch adhered to the vessel wall over the perforation.

In accordance with a further aspect of the present invention, there is provided a method and apparatus for introducing a vascular patch through a standard introducer cannula such as introducer 300 illustrated in FIG. 17. Following the completion of a percutaneous procedure such as an angiogram, PTCA, or other procedure, the introducer sheath 300 may be left in position within the artery 302. If the introducer sheath 300 has been removed following the primary procedure, a subsequent introducer sheath may then be inserted in accordance with conventional techniques.

The proximal manifold on an introducer sheath 300 is typically provided with a primary guidewire or catheter access port and a valved side port 309. The primary access port is generally provided with a valve such as a duck bill valve, a split septum valve or other structure for permitting passage of the guidewire or procedure catheter but minimizing the escape of blood.

Figure 28:
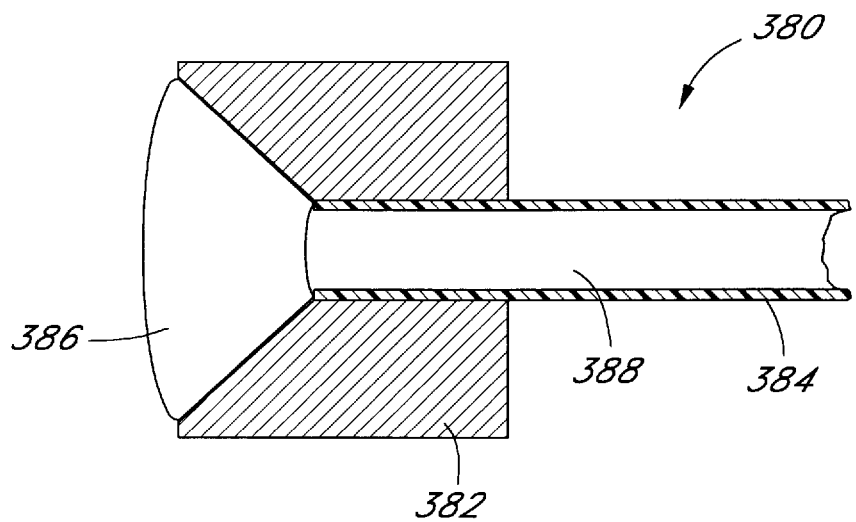
FIG. 28 is a cross-sectional schematic view of a funnel block and access tube in accordance with the present invention.

The present invention provides a bypass conduit for opening the valve in the primary access port to allow the passage of a patch and patch pusher into the artery. Referring to FIG. 28, a generally funnel-shaped bypass device 380 is illustrated. The bypass device 380 generally comprises a proximal block 382 and a distal tubular extension 384. Proximal block 382 is provided at its proximal end with a funnel shape opening 386 for providing access to a central lumen 388 in tubular extension 384. Preferably, the proximal block 382 is a medical grade plastic block which has been molded onto a proximal end of tubing 384. Tubing 384 may comprise a length of metallic walled hypotube.

The relative dimensions of the bypass device 380 can be varied as appropriate for the intended introducer 300 sheath with which it is to be used. In general, the axial length of the tube 384 extending distally from the block 382 will be within the range of from about 5 mm to about 25 mm. In a hypotube embodiment intended for use with currently marketed introducer sheaths the tubular body 384 will have an inside diameter of about 3 mm, and an outside diameter of about 3.5 mm.

The block 382 can take on any of a wide variety of configurations as will be apparent to those of skill in the art. Preferably, the block 382 is generally circular or rectangular in cross-sectional configuration, having a cross-sectional dimension of from about one to several centimeters to facilitate grasping the block between the thumb and forefinger. The funnel-shaped aperture 386 can also be varied in dimensions depending upon the size of the block 382.

In accordance with the present method, the sheath 300 is proximally withdrawn as has been discussed until the distal end of the introducer sheath 300 is positioned adjacent the outside of the artery. The guidewire is left in place extending through the introducer sheath 300 and into the artery. The bypass device 380 is installed within the manifold on introducer sheath 300 by advancing a distal end of the tubular body 384 over the guidewire and into the guidewire access port on the manifold and distally through the valve to maintain the valve in an open configuration. Blood flow is preferably stopped by digital pressure.

One convenient method of positioning the introducer sheath 300 is to proximally withdraw the sheath 300 until an abrupt drop in blood pressure is observed. Blood pressure can be monitored by connecting a conventional blood pressure monitor to the side port 309 of sheath 300. Alternatively, the side line valve can be opened to vent air and allow blood to run partway out the side line through side port 309. The valve is then closed so that the meniscus between the blood and trapped air in the line can be visually observed through the clear wall of the side line. While the distal end of the introducer sheath 300 is positioned within the artery, the meniscus can be seen to pulse back and forth in response to the arterial blood pressure, by compressing the air locked in the side line. At the time that the distal end of introducer sheath 300 is withdrawn from the artery, the visually apparent pulsing of the blood meniscus in the side line stops, thereby indicating the exit of the distal end of the sheath 300 from the artery.

Figure 29:
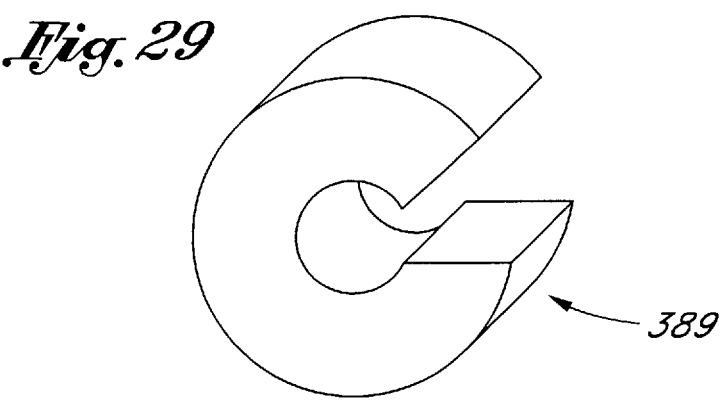
FIG. 29 is a perspective view of an introducer sheath marker clamp in accordance with the present invention.

Once the distal end of the sheath 300 has been positioned adjacent the outside wall of the artery, the sheath 300 may be held by the clinician or taped in position during the remaining steps of the procedure. However, to minimize the risk that the sheath 300 may move from its ready position, it may be desirable to provide a visual indicium or other indicator on the wall of the sheath 300 to provide a visual confirmation that the sheath has not been withdrawn or inserted relative to its ready position. For this purpose, any of a variety of visual indicium may be provided on the outside wall of the sheath 300. These include graduated markings, or slidable or movable clamp type structures which can be used to indicate the point on the sheath 300 where the sheath enters the percutaneous puncture. For example, referring to FIG. 29, there is disclosed one embodiment of a marker clamp 389 which can be clamped onto the sheath 300 and advanced axially along the sheath 300 until it comes into contact with the skin. Clamp 389 preferably comprises an elastomeric material with a memory, such that it can be press fit over the sheath 300 and will remain in position under the circumstances of the vascular patch procedure.

Once the bypass device 380 is in place within the manifold, a syringe or other fluid source is preferably introduced into the funnel 386 and normal saline or other solution is injected through the introducer sheath 300 to dilute the blood at the arterial wall. The present inventor has determined that reducing the concentration of red blood cells at the adhesion site improves adhesion between the vascular patch and the vessel wall.

Figure 25:
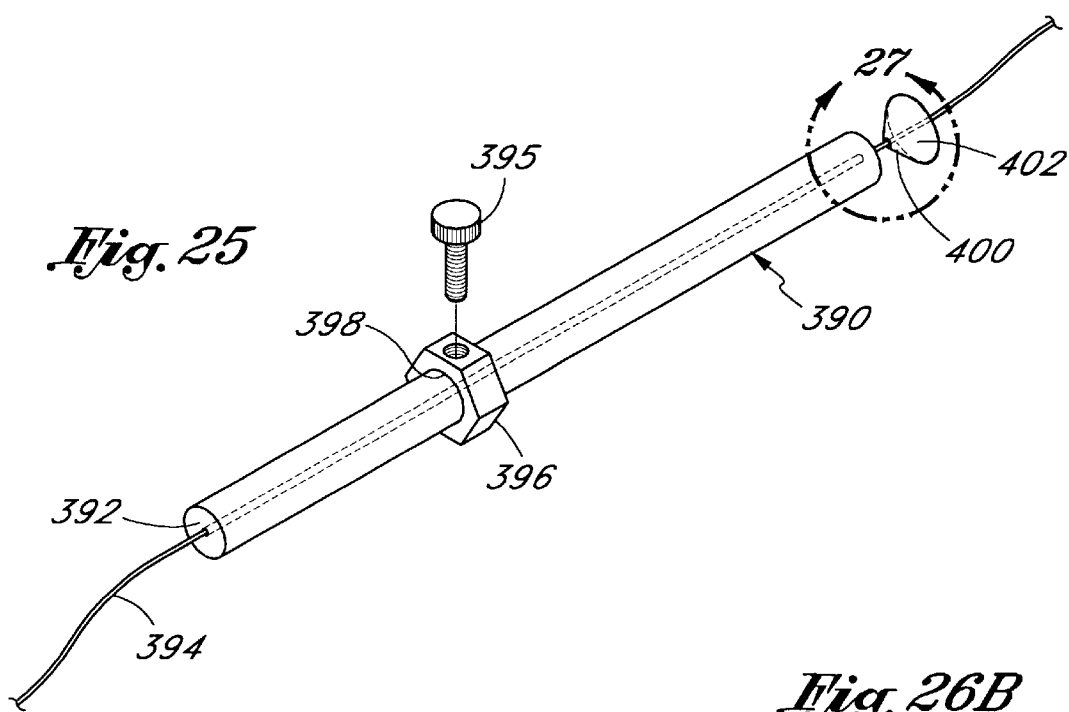
FIG. 25 is a perspective view of an alternate patch pusher assembly.

A vascular patch 400 and a quantity of vascular patch adhesive 402 is positioned onto a patch pusher assembly as illustrated in FIG. 25. Pusher 390 comprises a generally cylindrical tubular element, having an outside diameter sized to fit within the tubular element 384. In general, pusher 390 will have an outside diameter within the range of from about 2 mm to about 4 mm. The axial length of pusher 390 can be varied depending upon the intended application, but in a conventional femoral access puncture repair, the pusher 390 will have a length within the range of from about 5 cm to about 20 cm. A central lumen 392 extends axially throughout the length of pusher 390, for slidably receiving a guidewire 394. For use with a standard 0.035 inch diameter guidewire, the central lumen may have an inside diameter on the order of about 0.040 inches.

The commercially-available procedure cannulas such as introducer sheath 300 (FIG. 17) have a variety of lengths. The pusher 390 is therefore preferably long enough to be used with the longest of the standard lengths. In a preferred embodiment, a clamping block 396 having a central aperture 398 is axially slidably positioned on the pusher 390. Prior to the introduction of the cannula 300 into the patient, the pusher 390 is advanced through the cannula and clamping block 396 is located on the pusher 390 such that it limits distal travel of the pusher 390 so that the pusher 390 protrudes slightly beyond the distal end of the cannula 300. Clamping block 396 may be further provided with a fastening means such as a thumb screw 395 for clamping the block 396 onto the pusher 390. Alternatively, any of a variety of snap-fit or press-fit configurations for the clamping block 396 may be used.

The pusher 390 having a patch 400 and adhesive 402 thereon may then be advanced distally through the introducer sheath 300, with or without the guidewire 394 still present. Preferably, the guidewire 394 is left in place to help minimize the risk that the distal end of the introducer sheath 300 will wander from the arterial puncture site.

Figure 26A:
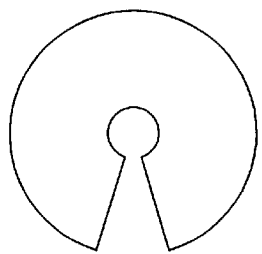
FIG. 26 is a schematic view of two vascular patch profiles.
Figure 26B:
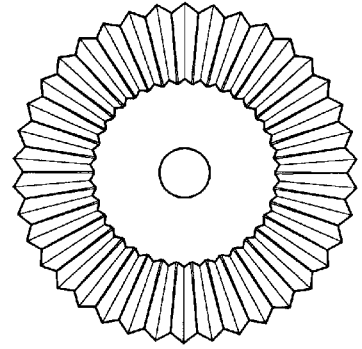
Figure 27:
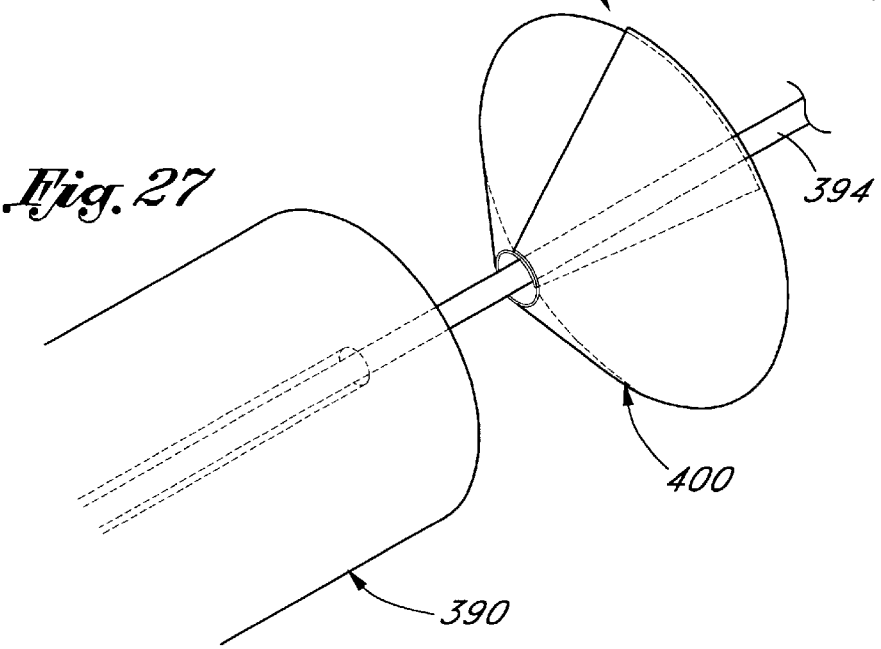
FIG. 27 is an enlargement of the distal end of the patch pusher illustrated in FIG. 25.

Due to the relatively small inside diameter of the conventional introducer sheath, it may be desirable to have patch which is capable of increasing in cross-sectional area from a reduced, introduction cross-sectional area to an enlarged, installed cross-sectional area. This may be accomplished by folding the patch or wrapping the patch in such a manner that it can fit within the inside lumen of introducer sheath 300 but will then expand upon exiting the distal end. For example, referring to FIG. 26, the patch may be constructed from a circular sheet of patch material (discussed previously) which has been provided with a central aperture for receiving the guidewire, and a radially extending slot. This patch material can be wrapped into a conical configuration to reduce its outside diameter for the installation process. Alternatively, the patch may be provided with a series of folds or corrugations in a cupcake wrapper-like fashion. Both of these configurations will have a generally concave side when configured in their reduced cross-sectional area form for introduction through introducer sheath 300. The patch is preferably positioned on the guidewire 394 and adjacent the pusher 390 such that the concave side faces towards the vessel wall. This concave side of the patch is preferably coated with or filled with a quantity of tissue adhesive 402 as has been discussed.

After the patch 400 has been advanced through the introducer cannula 300 to the vessel wall, a slight distal pressure on pusher 390 will cause the patch 400 to flatten out to a larger cross-sectional area and adhere to the vessel wall to seal the vascular puncture.

In accordance with a further aspect of the present invention, there is provided a method of sealing a vascular puncture using a bioabsorbable sealing tube. In accordance with this aspect of the invention, a patient is prepared following a vascular access procedure, such that the vascular puncture has a guidewire extending therefrom. The patient may be prepared by advancing a guidewire through the vascular access sheath and then removing the sheath following the conclusion of the prior procedure.

A bioabsorbable sealing tube is provided. The sealing tube is an elongate, generally rod-shaped body having a guidewire lumen extending axially therethrough. The inside diameter of the guidewire lumen is sufficient to slidably receive the guidewire. The outside diameter can vary, since in a preferred application it does not need to fit within a tubular introduction sheath. Outside diameters within the range of from about 0.1 inches to about 0.2 inches, or larger, can be used. The minimum outside diameter is typically governed by the physical properties of the particular bioabsorbable material used to construct the sealing tube.

In a preferred embodiment, at least the distal end of the bioabsorbable sealing tube is provided with a quantity of a tissue adhesive, such as a cyanoacrylate gel.

The distal end of the sealing tube is advanced over the proximal end of the guidewire, and thereafter advanced distally over the guidewire until the distal end of the sealing tube reaches the artery. The clinician can detect by tactile feedback when the tube has reached the artery, due to the resistance to further distal motion of the sealing tube. While holding the sealing tube against the artery, the guidewire may be removed. If a proximal end of the sealing tube projects proximally from the percutaneous opening, the proximal end of the tube may be cut off at or about the skin level. The tube and the skin puncture can thereafter be closed in accordance with conventional wound dressing techniques or by the application of a small amount of cyanoacrylate or other adhesive.

Kits are preferably provided, containing all or some of the components used in the puncture sealing procedure. The kit preferably includes a patch applicator, one or more vascular patches, and a unit dose of a cyanoacrylate based or other adhesive. A speculum may also be provided, for exposing a portion of the vessel wall around the vascular puncture. A tissue expander may also be provided, in embodiments where the speculum is not adapted for accomplishing that function as has been discussed. A guidewire may also be included. A kit for performing the bioabsorbable closure method may include a bioabsorbable sealing tube and a volume of adhesive. A guidewire may also be included.

Although the present invention has been described in terms of certain preferred embodiments, other embodiments can be readily devised by one with skill in the art in view of the foregoing, which will also use the basic concepts of the present invention. Accordingly, the scope of the present invention is to be defined by reference to the following claims.

What is claimed is:

1. A method of sealing a vascular perforation, comprising the steps of:
    identifying a patient having a vascular perforation and a tubular access sheath extending through the perforation and into the vessel;
    proximally withdrawing the access sheath until a distal end of the access sheath is positioned in the patient outside of the vessel;
    introducing a vascular patch into the proximal end of the access sheath;
    advancing the patch distally through the sheath; and
    positioning the patch against the vessel wall to seal the perforation.

2. A method of sealing a vascular perforation as in claim 1, further comprising the step of monitoring blood pressure through the access sheath during said proximally withdrawing step.

3. A method of sealing a vascular perforation as in claim 2, wherein said proximally withdrawing step comprises proximally withdrawing the access sheath until an abrupt drop in blood pressure is measured at the distal end of the sheath.

4. A method of sealing a vascular perforation as in claim 1, wherein said tubular access sheath comprises a tubular introducer sheath.

5. A method of sealing a vascular perforation as in claim 1, further comprising the step of advancing a guidewire distally through the tubular access sheath and into the vessel.

6. A method of sealing a vascular perforation as in claim 5, wherein the patch is provided with a guidewire aperture therein, and said introducing a vascular patch step comprises advancing the patch distally along the guidewire.

7. A method of sealing a vascular perforation as in claim 6, further comprising the step of applying an adhesive to the patch for securing the patch to the vessel.

8. A method of sealing a vascular perforation as in claim 1, further comprising the step of providing a vascular patch applicator having an axially extending guidewire lumen therethrough, and wherein the advancing the patch distally through the sheath step comprises mounting the applicator on the proximal end of the guidewire and advancing the applicator distally over the guidewire to advance the patch towards the vessel.

9. A method of sealing a vascular perforation, comprising the steps of:
    identifying a patient having a vascular perforation and a guidewire extending therethrough;
    providing a vascular patch having an aperture therethrough:
    providing a bioabsorbable sealing tube having a central guidewire lumen extending therethrough;
    mounting the sealing tube and the vascular patch coaxially on the guidewire;
    advancing the sealing tube distally over the guidewire until a distal end of the sealing tube encounters resistance to distal progress as a result of the vessel wall and so that the vascular patch advances toward the vessel wall; and
    withdrawing the guidewire from the patient.

10. A method of sealing a vascular perforation as in claim 9, further comprising the step of severing a proximal portion of the sealing tube following the advancing step.

11. A method of percutaneous transluminal catheterization and inhibiting arterial bleeding at the arterial perforation site following the procedure, comprising the steps of:
    perforating an artery to provide access to the arterial system;
    advancing an introducer sheath through the perforation and into the artery;
    introducing a catheter through the introducer sheath and into the artery;
    advancing the catheter to a preselected treatment or diagnostic site;
    withdrawing the catheter from the artery;
    withdrawing the introducer sheath from the perforation so that a distal end of the introducer sheath is positioned in the patient outside the artery; and
    advancing a patch having a tissue adhesive thereon through the introducer sheath to seal the perforation.

12. A method as in claim 11, wherein the introducer sheath has a distal end, and wherein the withdrawing the introducer sheath step comprises withdrawing the introducer sheath a sufficient distance that the distal end of the introducer sheath is outside of but remains adjacent to the artery.

13. A method of sealing a vascular perforation, comprising the steps of:
   identifying a patient having a vascular perforation and a guidewire extending through the perforation and into the vessel;
   providing a tissue expander having a generally tubular distal end which is enlargeable from a first, introduction cross-sectional area to a second, enlarged cross-sectional area;
   advancing the tissue expander distally through adjacent tissue to expose the vascular perforation;
   introducing a vascular patch into the proximal end of the tissue expander;
   advancing the patch distally through the tissue expander;
   positioning the patch against the vessel wall to seal the perforation.

14. A method as in claim 14, wherein the tissue expander comprises an elongate, generally cylindrical tubular structure.

15. A method as in claim 13, further comprising the step of expanding the tissue expander from the first cross sectional area to the second cross sectional area prior to the introducing step.

16. A method of sealing a vascular perforation, comprising the steps of:
   identifying a patient having a vascular perforation and a tubular access sheath extending through the perforation and into the vessel;
   monitoring blood pressure through the access sheath while proximally withdrawing the access sheath until a distal end of the access sheath is positioned in the patient outside of the vessel;
   introducing a vascular patch into the proximal end of the access sheath;
   advancing the patch distally through the sheath; and
   positioning the patch against the vessel wall to seal the perforation.

17. A method of sealing a vascular perforation as in claim 16, wherein said proximally withdrawing step comprises proximally withdrawing the access sheath until an abrupt drop in blood pressure is measured at the distal end of the sheath.

18. A method of sealing a vascular perforation as in claim 16, wherein said tubular access sheath comprises a tubular introducer sheath.

19. A method of sealing a vascular perforation as in claim 16, further comprising the step of advancing a guidewire distally through the tubular access sheath and into the vessel.

20. A method of sealing a vascular perforation as in claim 19, wherein the patch is provided with a guidewire aperture therein, and said introducing a vascular patch step comprises advancing the patch distally along the guidewire.

21. A method of sealing a vascular perforation as in claim 20, further comprising the step of applying an adhesive to the patch for securing the patch to the vessel.

22. A method of sealing a vascular perforation as in claim 16, further comprising the step of providing a vascular patch applicator having an axially extending guidewire lumen therethrough, and wherein the advancing the patch distally through the sheath step comprises mounting the applicator on the proximal end of the guidewire and advancing the applicator distally over the guidewire to advance the patch towards the vessel.

* * * * *

UNITED STATES PATENT AND TRADEMARK OFFICE
CERTIFICATE OF CORRECTION

PATENT NO. : 5,843,124
DATED : December 1, 1998
INVENTOR(S) : Julius G. Hammerslag It is certified that error appears in the above-identified patent and that said Letters Patent is hereby corrected as shown below:

In column 31, line 23, "as in claim 14" should be --as in claim 13--.

Signed and Sealed this

First Day of February, 2000

Attest:

Q. TODD DICKINSON

*Attesting Officer*   *Acting Commissioner of Patents and Trademarks*